United States Patent
Bryan et al.

(12)

(10) Patent No.: US 6,204,294 B1
(45) Date of Patent: Mar. 20, 2001

(54) IL-8 RECEPTOR ANTAGONISTS

(75) Inventors: Deborah Lynn Bryan, West Chester; John Gerald Gleason, Downingtown; Katherine L. Widdowson, King of Prussia, all of PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/230,977
(22) PCT Filed: Aug. 15, 1997
(86) PCT No.: PCT/US97/14581
§ 371 Date: Feb. 4, 1999
§ 102(e) Date: Feb. 4, 1999
(87) PCT Pub. No.: WO98/06397
PCT Pub. Date: Feb. 19, 1998

Related U.S. Application Data

(60) Provisional application No. 60/023,414, filed on Aug. 15, 1996.

(51) Int. Cl.[7] .................................................. A61K 31/155
(52) U.S. Cl. ............................................ 514/609; 514/634
(58) Field of Search ...................................... 514/634, 609

(56) References Cited

U.S. PATENT DOCUMENTS

| 4,269,837 | * | 5/1981 | Watt et al. ............................ 424/246 |
| 5,084,369 | * | 1/1992 | Tanaka et al. ....................... 430/110 |
| 5,214,208 | * | 5/1993 | Tanaka et al. ....................... 564/236 |
| 5,371,086 | | 12/1994 | Takemoto et al. . |
| 5,401,758 | | 3/1995 | Atwal et al. . |
| 5,567,722 | | 10/1996 | Humphrey et al. . |
| 5,792,444 | * | 8/1998 | Fischman et al. .................. 424/1.69 |

FOREIGN PATENT DOCUMENTS

387769 * 9/1990 (EP) .

OTHER PUBLICATIONS

Manley, P.W., "Structure–Activity Studies of Potassium Channel Opening in Pinacidil–Type Cyanoguanidines etc.", *J. Med. Chem.*, 35(12), pp. 2327–2340 (1992).

\* cited by examiner

*Primary Examiner*—William R. A. Jarvis
*Assistant Examiner*—Vickie Kim
(74) *Attorney, Agent, or Firm*—Soma G. Simon; Dara L. Dinner; Charles M. Kinzig

(57) ABSTRACT

This invention relates to novel compounds of Formula (1), pharmaceutical compositions and their use in the treatment of disease states mediated by the chemokine, Interleukins-8 (IL-8).

10 Claims, No Drawings

IL-8 RECEPTOR ANTAGONISTS

RELATED APPLICATIONS:

This application is the § 371 national stage entry of PCT/US97/14581, filed Aug. 15, 1997 which claims the benefit of provisional application 60/023,414, filed Aug. 15, 1996.

FIELD OF THE INVENTION

This invention relates to novel guanidine containing compounds, pharmaceutical compositions, processes for their preparation, and use thereof in treating IL-8, GROα, GROβ, GROγ, ENA-78, and NAP-2 mediated diseases.

BACKGROUND OF THE INVENTION

Many different names have been applied to Interleukin-8 (IL-8), such as neutrophil attractant/activation protein-1 (NAP-1), monocyte derived neutrophil chemotactic factor (MDNCF), neutrophil activating factor (NAF), and T-cell lymphocyte chemotactic factor. Interleukin-8 is a chemoattractant for neutrophils, basophils, and a subset of T-cells. It is produced by a majority of nucleated cells including macrophages, fibroblasts, endothelial and epithelial cells exposed to TNF, IL-1α, IL-1β or LPS, and by neutrophils themselves when exposed to LPS or chemotactic factors such as FMLP. M. Baggiolini et al, *J. Clin. Invest.* 84, 1045 (1989); J. Schroder et al, *J. Immunol.* 139, 3474 (1987) and *J. Immunol.* 144, 2223 (1990); Strieter, et al, *Science* 243, 1467 (1989) and *J. Biol. Chem.* 264, 10621 (1989); Cassatellaet al, *J. Immunol.* 148, 3216 (1992).

GROα, GROβ, GROγ and NAP-2 also belong to the chemokine α family. Like IL-8 these chemokines have also been referred to by different names. For instance GROα, β, γ have been referred to as MGSAα, β and γ respectively (Melanoma Growth Stimulating Activity), see Richmond et al, *J. Cell Physiology* 129, 375 (1986) and Chang et al, *J. Immunol* 148, 451 (1992). All of the chemokines of the α-family which possess the ELR motif directly preceding the CXC motif bind to the IL-8 B receptor.

IL-8, GROα, GROβ, GROγ and NAP-2 stimulate a number of functions in vitro. They have all been shown to have chemoattractant properties for neutrophils, while IL-8 and GROα have demonstrated T-lymphocytes, and basophiles chemotactic activity. In addition IL-8 can induce histamine release from basophils from both normal and atopic individuals GRO-α and IL-8 can in addition, induce lysozomal enzyme release and respiratory burst from neutrophils. IL-8 has also been shown to increase the surface expression of Mac-1 (CD11b/CD18) on neutrophils without de novo protein synthesis. This may contribute to increased adhesion of the neutrophils to vascular endothelial cells. Many known diseases are characterized by massive neutrophil infiltration. As IL-8, GROα, GROβ, GROγ and NAP-2 promote the accumulation and activation of neutrophils, these chemokines have been implicated in a wide range of acute and chronic inflammatory disorders including psoriasis and rheumatoid arthritis, Baggiolini et al, *FEBS Lett.* 307, 97 (1992); Miller et al, *Crit. Rev. Immunol.* 12, 17 (1992); Oppenheim et al, *Annu. Rev. Immunol.* 9, 617 (1991); Seitz et al., *J. Clin. Invest.* 87, 463 (1991); Miller et al., *Am. Rev. Respir. Dis.* 146, 427 (1992); Donnely et al., *Lancet* 341, 643 (1993). In addition the ELR chemokines (those containing the amino acids ELR motif just prior to the CXC motif) have also been implicated in angiostasis. Strieter et al, *Science* 258, 1798 (1992).

In vitro, IL-8, Groα, GROβ, GROγ and NAP-2 induce neutrophil shape change, chemotaxis, granule release, and respiratory burst, by binding to and activating receptors of the seven-transmembrane, G-protein-linked family, in particular by binding to IL-8 receptors, most notably the B-receptor. Thomas et al., *J. Biol. Chem.* 266, 14839 (1991); and Holmes et al., *Science* 253, 1278 (1991). The development of non-peptide small molecule antagonists for members of this receptor family has precedent. For a review see R. Freidinger in: *Progress in Drug Research*, Vol. 40, pp. 33–98, Birkhauser Verlag, Basel 1993. Hence, the IL-8 receptor represents a promising target for the development of novel anti-inflammatory agents.

Two high affinity human IL-8 receptors (77% homology) have been characterized: IL-8Rα, which binds only IL-8 with high affinity, and IL-8Rβ, which has high affinity for IL-8 as well as for GRO-α, GROβ, GROγ and NAP-2. See Holmes et al., supra; Murphy et al., *Science* 253, 1280 (1991); Lee et al., *J. Biol. Chem.* 267, 16283 (1992); LaRosa et al., *J. Biol. Chem.* 267, 25402 (1992); and Gayle et al., *J. Biol. Chem.* 268, 7283 (1993).

There remains a need for treatment, in this field, for compounds which are capable of binding to the IL-8 α or β receptor. Therefore, conditions associated with an increase in IL-8 production (which is responsible for chemotaxis of neutrophil and T-cells subsets into the inflammatory site) would benefit by compounds which are inhibitors of IL-8 receptor binding.

SUMMARY OF THE INVENTION

This invention provides for a method of treating a chemokine mediated disease, wherein the chemokine is one which binds to an IL-8 α or β receptor and which method comprises administering an effective amount of a compound of Formula (I) or a pharmaceutically acceptable salt thereof. In particular the chemokine is IL-8.

This invention also relates to a method of inhibiting the binding of IL-8 to its receptors in a mammal in need thereof which comprises administering to said mammal an effective amount of a compound of Formula (I).

Compounds of Formula (I) useful in the present invention are represented by the structure:

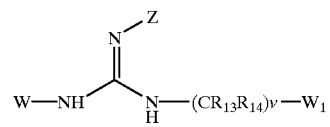

wherein

Z is cyano, $OR_{11}$, $C(O)NR_{15}R_{16}$, $R_{18}$, $C(O)R_{11}$, $C(O)OR_{11}$, or $S(O)_2R_{17}$;

R is any functional moiety having an ionizable hydrogen and a pKa of 10 or less;

$R_1$ is independently selected from hydrogen; halogen; nitro; cyano; halosubstituted $C_{1-10}$ alkyl; $C_{1-10}$ alkyl; $C_{2-10}$ alkenyl; $C_{1-10}$ alkoxy; halosubstituted $C_{1-10}$ alkoxy; azide; $(CR_8R_8)q$ $S(O)_tR_4$; hydroxy; hydroxy $C_{1-4}$alkyl; aryl; aryl $C_{1-4}$ alkyl; aryloxy; aryl $C_{1-4}$ alkyloxy; heteroaryl; heteroarylalkyl; heterocyclic, heterocyclic $C_{1-4}$alkyl; heteroaryl $C_{1-4}$ alkyloxy; aryl $C_{2-10}$ alkenyl; heteroaryl $C_{2-10}$ alkenyl; heterocyclic $C_{2-10}$ alkenyl; $(CR_8R_8)qNR_4R_5$; $C_{2-10}$ alkenyl $C(O)$ $NR_4R_5$; $(CR_8R_8)q$ $C(O)NR_4R_5$; $(CR_8R_8)q$ $C(O)$ $NR_4R_{10}$; $S(O)_3H$; $S(O)_3R_8$; $(CR_8R_8)q$ $C(O)R_{11}$; $C_{2-10}$ alkenyl C(O)R$_{11}$; C$_{2-10}$ alkenyl C(O)OR$_{11}$; (CR$_8$R$_8$)q C(O)OR$_{12}$; (CR$_8$R$_8$)q OC(O) R$_{11}$; (CR$_8$R$_8$)qNR$_4$C(O)R$_{11}$, (CR$_8$R$_8$)q NHS(O)$_2$R$_{19}$, (CR$_8$R$_8$)q S(O)$_2$NR$_4$R$_5$; or two R$_1$ moieties together may form O—(CH$_2$)$_s$O— or a 5 to 6 membered saturated or unsaturated ring;

q is 0, or an integer having a value of 1 to 10;

t is 0, or an integer having a value of 1 or 2;

s is an integer having a value of 1 to 3;

v is 0, or an integer having a value of 1 to 4;

R$_4$ and R$_5$ are independently hydrogen, optionally substituted C$_{1-4}$ alkyl, optionally substituted aryl, optionally substituted aryl C$_{1-4}$alkyl, optionally substituted heteroaryl, optionally substituted heteroaryl C$_{1-4}$alkyl, heterocyclic, heterocyclic C$_{1-4}$ alkyl, or R$_4$ and R$_5$ together with the nitrogen to which they are attached form a 5 to 7 member ring which may optionally comprise an additional heteroatom selected from oxygen, nitrogen or sulfur;

Y is independently selected from hydrogen; halogen; nitro; cyano; halosubstituted C$_{1-10}$ alkyl; C$_{1-10}$ alkyl; C$_{2-10}$ alkenyl; C$_{1-10}$ alkoxy; halosubstituted C$_{1-10}$ alkoxy; azide; (CR$_8$R$_8$)q S(O)$_t$R$_4$; hydroxy; hydroxyC$_{1-4}$alkyl; aryl; aryl C$_{1-4}$ alkyl; aryloxy; arylC$_{1-4}$ alkyloxy; heteroaryl; heteroarylalkyl; heteroaryl C$_{1-4}$ alkyloxy; heterocyclic, heterocyclic C$_{1-4}$alkyl; aryl C$_{2-10}$ alkenyl; heteroaryl C$_{2-10}$ alkenyl; heterocyclic C$_{2-10}$ alkenyl; (CR$_8$R$_8$)q NR$_4$R$_5$; C$_{2-10}$ alkenyl C(O)NR$_4$R$_5$; (CR$_8$R$_8$)q C(O)NR$_4$R$_5$; (CR$_8$R$_8$)q C(O)NR$_4$R$_{10}$; S(O)$_3$H; S(O)$_3$R$_8$; (CR$_8$R$_8$)q C(O)R$_{11}$; C$_{2-10}$ alkenyl C(O)R$_{11}$; C$_{2-10}$ alkenyl C(O)OR$_{11}$; C(O)R$_{11}$; (CR$_8$R$_8$)q C(O)OR$_{12}$; (CR$_8$R$_8$)q OC(O) R$_{11}$; (CR$_8$R$_8$)q NR$_4$C(O)R$_{11}$, (CR$_8$R$_8$)q NHS(O)$_2$R$_d$, (CR$_8$R$_8$)q S(O)$_2$NR$_4$R$_5$; or two Y moieties together may form O—(CH$_2$)$_s$O— or a 5 to 6 membered saturated or unsaturated ring;

n is an integer having a value of 1 to 3;

m is an integer having a value of 1 to 3;

R$_6$ and R$_7$ are independently hydrogen or a C$_{1-4}$ alkyl group; or R$_6$ and R$_7$ together with the nitrogen to which they are attached form a 5 to 7 member ring which ring may optionally contain an additional heteroatom selected from oxygen, nitrogen or sulfur;

R$_8$ is independently selected from hydrogen or C$_{1-4}$ alkyl;

R$_{10}$ is C$_{1-10}$ alkyl C(O)$_2$R$_8$;

R$_{11}$ is hydrogen, C$_{1-4}$ alkyl, optionally substituted aryl, optionally substituted aryl C$_{1-4}$alkyl, optionally substituted heteroaryl, optionally substituted heteroarylC$_{1-4}$alkyl, optionally substituted heterocyclic, or optionally substituted heterocyclicC$_{1-4}$alkyl;

R$_{12}$ is hydrogen, C$_{1-10}$ alkyl, optionally substituted aryl or optionally substituted arylalkyl;

R$_{13}$ and R$_{14}$ are independently hydrogen, optionally substituted C$_{1-4}$ alkyl or one of R$_{13}$ and R$_{14}$ may be optionally substituted aryl;

R$_{15}$ and R$_{16}$ are independently hydrogen, optionally substituted C$_{1-4}$ alkyl, optionally substituted aryl, optionally substituted aryl C$_{1-4}$alkyl, optionally substituted heteroaryl, optionally substituted heteroarylC$_{1-4}$alkyl, optionally substituted heterocyclic, optionally substituted heterocyclicC$_{1-4}$alkyl, or R$_{15}$ and R$_{16}$ may together with the nitrogen to which they are attached form a 5 to 7 member ring optionally containing an additional heteroatom selected from oxygen, nitrogen, or sulfur;

R$_{17}$ is C$_{1-4}$ alkyl, NR$_{15}$R$_{16}$, OR$_{11}$, optionally substituted aryl, optionally substituted aryl C$_{1-4}$alkyl, optionally substituted heteroaryl, optionally substituted heteroarylC$_{1-4}$alkyl, optionally substituted heterocyclic, or optionally substituted heterocyclicC$_{1-4}$ alkyl;

R$_{18}$ is optionally substituted C$_{1-4}$ alkyl, optionally substituted aryl, optionally substituted aryl C$_{1-4}$alkyl, optionally substituted heteroaryl, optionally substituted heteroarylC$_{1-4}$alkyl, optionally substituted heterocyclic, or optionally substituted heterocyclicC$_{1-4}$ alkyl;

R$_{19}$ is C$_{1-4}$alkyl, aryl, arylalkyl, heteroaryl, heteroarylC$_{1-4}$alkyl, heterocyclic, or heterocyclicC$_{1-4}$alkyl, wherein the all of these moieties may be optionally substituted;

R$_d$ is NR$_6$R$_7$, alkyl, arylC$_{1-4}$ alkyl, arylC$_{2-4}$ alkenyl, heteroaryl, hetroaryl-C$_{1-4}$alkyl, heteroarylC$_{2-4}$ alkenyl, heterocyclic, heterocyclicC$_{1-4}$ alkyl, wherein the alkyl, aryl, arylalkyl, heteroaryl, heteroaryl alkyl, heterocyclic, and heterocyclic alkyl rings may be optionally substituted;

W is 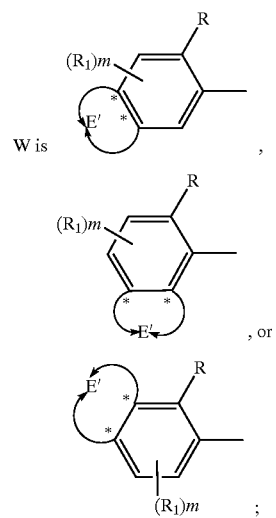

the E' containing ring is optionally selected from

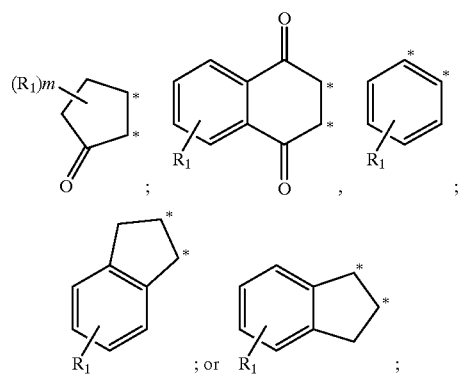

the asterix * denoting point of attachment of the ring;

-continued

W₁ is 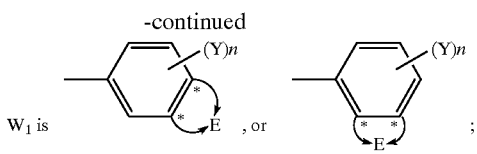

the E containing ring is optionally selected from

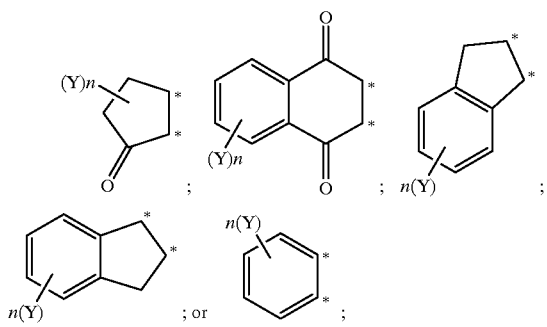

the asterix * denoting point of attachment of the ring;

or a pharmaceutically acceptably salt thereof.

DETAILED DESCRIPTION OF THE INVENTION

The compounds of Formula (I) may also be used in association with the veterinary treatment of mammals, other than humans, in need of inhibition of IL-8 or other chemokines which bind to the IL-8α and β receptors. Chemokine mediated diseases for treatment, therapeutically or prophylactically, in animals include disease states such as those noted herein in the Methods of Treatment section.

In compounds of Formula (I), W is suitably

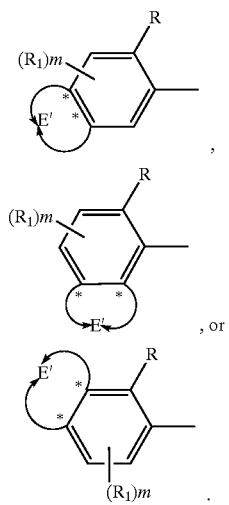

The E' containing ring, denoted by its point of attachment through the asterix (*) may optionally be present. If if it is not present the ring is a phenyl moiety which is substituted by the $R_1$ terms as shown. The E ring may be substituted by the $R_1$ moiety in any ring, saturated or unsaturated, and is shown for purposes herein substituted only in the unsaturated ring(s).

R is suitably any functional moiety which provides an ionizable hydrogen having a pKa of 10 or less, preferably from about 3 to 9, more preferably from about 3 to 7. Such functional groups include, but are not limited to, hydroxy, carboxylic acid, thiol, $—SR_2$, $—OR_2$, $—NH—C(O)R_a$, $—C(O)NR_6R_7$, a substituted sulfonamides of the formula $—NHS(O)_2R_b$, $—S(O)_2NHR_c$, $NHC(X_2)NHR_b$, or a tetrazolyl; wherein $X_2$ is oxygen or sulfur, preferably oxygen. Preferably, the functional group is other than a sulfonic acid, either directly or as a substituent group on the aryl, heteroaryl, or heterocyclic moiety ring, such as in $SR_2$ or $OR_2$. More preferably R is OH, SH, or $NHS(O)_2R_b$.

Suitably, $R_2$ is a substituted aryl, heteroaryl, or heterocyclic moiety which ring has the functional moiety providing the ionizable hydrogen having a pKa of 10 or less.

Suitably, $R_{6'}$ and $R_{7'}$ are hydrogen, $C_{1-4}$ alkyl, aryl, $arylC_{1-4}alkyl$, $arylC_{2-4}alkenyl$, heteroaryl, $heteroarylC_{1-4}$ alkyl, $heteroarylC_{2-4}$ alkenyl, heterocyclic, heterocyclic $C_{1-4}alkyl$, heterocyclic $C_{2-4}alkenyl$ moiety, all of which may be optionally substituted one to three times independently by halogen; nitro; halosubstituted $C_{1-4}$ alkyl, such as $CF_3$; $C_{1-4}$ alkyl, such as methyl; $C_{1-4}$ alkoxy, such as methoxy; $NR_9C(O)R_a$; $C(O)NR_6R_7$; $S(O)_3H$; or $C(O)OC_{1-4}$ alkyl, provided that only one of $R_{6'}$ and $R_{7'}$ are hydrogen, but not both.

Suitably, $R_6$ and $R_7$ are independently hydrogen or a $C_{1-4}$ alkyl group, or $R_6$ and $R_7$ together with the nitrogen to which they are attached form a 5 to 7 member ring which ring may optionally contain an additional heteroatom which heteroatom is selected from oxygen, nitrogen or sulfur. This heteroring may be optionally substituted as defined herein.

Suitably $R_a$ is an aryl, $arylC_{1-4}alkyl$, heteroaryl, $heteroarylC_{1-4}alkyl$, heterocyclic, or a heterocyclic $C_{1-4}alkyl$ moiety, all of which may be optionally substituted, as defined herein below.

Suitably, $R_b$ is a $NR_6R_7$, alkyl, aryl, $arylC_{1-4}alkyl$, $arylC_{2-4}$ alkenyl, heteroaryl, $heteroarylC_{1-4}alkyl$, $heteroarylC_{2-4}$ alkenyl, heterocyclic, heterocyclic $C_{1-4}alkyl$, heterocyclic $C_{2-4}alkenyl$ moiety, or camphor, all of which may be optionally substituted one to three times independently by halogen; nitro; halosubstituted $C_{1-4}$ alkyl, such as $CF_3$; $C_{1-4}$ alkyl, such as methyl; $C_{1-4}$ alkoxy, such as methoxy; $NR_9C(O)R_a$; $C(O)NR_6R_7$; $S(O)_3H$; or $C(O)OC_{1-4}$ alkyl. $R_b$ is preferably an optionally substituted phenyl, benzyl, or styryl. When $R_b$ is a heteroaryl preferably it is an optionally substituted thiazole, optionally substituted thienyl, or optionally substituted quinolinyl ring.

Suitably $R_9$ is hydrogen or a $C_{1-4}$ alkyl, preferably hydrogen. Preferably, when the substituent group is $NR_9C(O)R_a$, then $R_a$ is preferably an alkyl group, such as methyl.

Suitably $R_c$ is hydrogen, alkyl, aryl, $arylc_{1-4}alkyl$, $arylC_{1-4}$ alkenyl, heteroaryl, $heteroarylC_{1-4}alkyl$, $heteroarylC_{1-4}$ alkenyl, heterocyclic, heterocyclic $C_{1-4}alkyl$, or heterocyclic $C_{1-4}alkenyl$ moiety, all of which may be optionally substituted one to three times independently by halogen, nitro, halosubstituted $C_{1-4}$ alkyl, $C_{1-4}$ alkyl, $C_{1-4}$ alkoxy, $NR_9C(O)R_a$, $C(O)NR_6R_7$, $S(O)_3H$, or $C(O)OC_{1-4}$ alkyl, wherein $R_9$ is hydrogen or a $C_{1-4}$ alkyl. Preferably, $R_c$ is an optionally substituted phenyl.

When R is an $OR_2$ or $SR_2$ moiety it is recognized by one of skill in the art that the aryl ring must, therefore, contain the required ionizable hydrogen. The aryl ring may also be additionally substituted, independently, by one to three groups, which groups may also contain an additional ionizable group, and which include but are not limited to, halogen, nitro, halosubstituted $C_{1-4}$ alkyl, $C_{1-4}$ alkyl, $C_{1-4}$ alkoxy, hydroxy, SH, $—C(O)NR_6R_7$, $—NH—C(O)R_a$, $—NHS(O)_2R_b$, $S(O)_2NR_6R_7$, $C(O)OR_8$, or a tetrazolyl ring.

In compounds of Formula (I), suitably $R_1$ is independently selected from hydrogen; halogen; nitro; cyano; halosubstituted $C_{1-10}$ alkyl, such as $CF_3$; $C_{1-10}$ alkyl, such as methyl, ethyl, isopropyl, or n-propyl; $C_{2-10}$ alkenyl; $C_{1-10}$ alkoxy, such as methoxy, or ethoxy; halosubstituted $C_{1-10}$ alkoxy, such as trifluoromethoxy; azide; $(CR_8R_8)q\ S(O)_tR_4$, wherein t is 0, 1 or 2; hydroxy; hydroxy $C_{1-4}$alkyl, such as methanol or ethanol; aryl, such as phenyl or naphthyl; aryl $C_{1-4}$ alkyl, such as benzyl; aryloxy, such as phenoxy; aryl $C_{1-4}$ alkyloxy, such as benzyloxy; heteroaryl; heteroarylalkyl; heteroaryl $C_{1-4}$ alkyloxy; aryl $C_{2-10}$ alkenyl; heteroaryl $C_{2-10}$ alkenyl; heterocyclic $C_{2-10}$ alkenyl; $(CR_8R_8)qNR_4R_5$; $C_{2-10}$ alkenyl $C(O)NR_4R_5$; $(CR_8R_8)q\ C(O)NR_4R_5$; $(CR_8R_8)q\ C(O)NR_4R_{10}$; $S(O)_3H$; $S(O)_3R_8$; $(CR_8R_8)q\ C(O)R_{11}$; $C_{2-10}$ alkenyl $C(O)R_{11}$; $C_{2-10}$ alkenyl $C(O)OR_{11}$; $C(O)R_{11}$; $(CR_8R_8)q\ C(O)OR_{12}$; $(CR_8R_8)qOC(O)R_{11}$; $(CR_8R_8)q\ NR_4C(O)R_{11}$, $(CR_8R_8)q\ NHS(O)_2R_{19}$, $(CR_8R_8)qS(O)_2NR_4R_5$; or two $R_1$ moieties together may form $O-(CH_2)_sO-$ or a 5 to 6 membered saturated or unsaturated ring; and s is an integer having a value of 1 to 3. The aryl, heteroaryl, and heterocyclic containing moieites may be optionally substituted as defined herein below.

Suitably, q is 0, or an integer having a value of 1 to 10.

When $R_1$ forms a dioxybridge, s is preferably 1. When $R_1$ forms an additional saturated or unsaturated 5 to 6 membered ring, it is preferably 6 membered ring with unsaturation, resulting in a naphthylene ring system. These rings may be substituted independently, 1 to 3 times by the other $R_1$ moieties as defined above.

Suitably, $R_4$ and $R_5$ are independently hydrogen, optionally substituted $C_{1-4}$ alkyl, optionally substituted aryl, optionally substituted aryl $C_{1-4}$alkyl, optionally substituted heteroaryl, optionally substituted heteroaryl $C_{1-4}$alkyl, heterocyclic, heterocyclic$C_{1-4}$ alkyl, or $R_4$ and $R_5$ together with the nitrogen to which they are attached form a 5 to 7 member ring which may optionally comprise an additional heteroatom selected from O/N/S.

$R_8$ is suitably independently selected from hydrogen or $C_{1-4}$ alkyl.

$R_{10}$ is suitably $C_{1-10}$ alkyl $C(O)_2R_8$, such as $CH_2C(O)_2H$ or $CH_2C(O)_2CH_3$.

$R_{11}$ is suitably hydrogen, $C_{1-4}$ alkyl, aryl, aryl $C_{1-4}$ alkyl, heteroaryl, heteroaryl $C_{1-4}$alkyl, heterocyclic, or heterocyclic $C_{1-4}$alkyl.

$R_{12}$ is suitably hydrogen, C1-10 alkyl, optionally substituted aryl or optionally substituted arylalkyl.

$R_{19}$ is $C_{1-4}$alkyl, aryl, arylalkyl, heteroaryl, heteroaryl$C_{1-4}$ alkyl, heterocyclic, or heterocyclic$C_{1-4}$alkyl, wherein the all of these moieties may be optionally substituted;

Preferably $R_1$ is halogen, cyano, nitro, $CF_3$, $C(O)NR_4R_5$, alkenyl $C(O)NR_4R_5$, $C(O)\ R_4R_{10}$, alkenyl $C(O)OR_{12}$, heteroaryl, heteroarylalkyl, heteroaryl alkenyl, or $S(O)NR_4R_5$, and preferably $R_4$ and $R_5$ are both hydrogen or one is phenyl. A preferred ring substitution for $R_1$ is in the 4-position of the phenyl ring.

When R is OH, SH or $NSO_2R_b$, than $R_1$ is preferably substituted in the 3-position, the 4-position or di substituted in the 3,4-position. The substituent group is suitably an electron withdrawing moiety. Preferably when R is OH, SH or $NSO_2R_b$, than $R_1$ is nitro, halogen, cyano, trifluoromethyl group, $C(O)NR_4R_5$.

When R is carboxylic acid, than $R_1$ is preferably hydrogen, or $R_1$ is preferably substituted in the 4-position, more preferably substituted by trifluoromethyl or chloro.

In compounds of Formula (I), suitably $R_{13}$ and $R_{14}$ are independently hydrogen, optionally substituted $C_{1-4}$ alkyl which may be straight or branched as defined herein, or one of $R_{13}$ and $R_{14}$ are an optionally substituted aryl; v is 0, or an integer having a value of 1 to 4.

When $R_{13}$ or $R_{14}$ are an optionally substituted alkyl, the alkyl moiety may be substituted one to three times independently by halogen; halosubstituted $C_{1-4}$ alkyl such as trifluromethyl; hydroxy; hydroxy $C_{1-4}$alkyl, $C_{1-4}$ alkoxy; such as methoxy, or ethoxy, halosubstituted $C_{1-10}$ alkoxy, $S(O)_tR_4$; aryl; $NR_4R_5$; $NHC(O)R_4$; $C(O)NR_4R_5$; or $C(O)OR_8$.

In compounds of Formula (I), $W_1$ is suitably

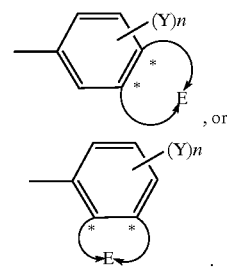

The E containing ring, denoted by its point of attachment through the asterix (*) may optionally be present. If if it is not present the ring is a phenyl moiety which is substituted by the Y terms as shown herein. The E ring may be substituted by the Y moiety in any ring, saturated or unsaturated, and is shown for purposes herein substituted only in the unsaturated ring(s).

Suitably, Y is independently selected from hydrogen; halogen; nitro; cyano; halosubstituted $C_{1-10}$ alkyl; $C_{1-10}$ alkyl; $C_{2-10}$ alkenyl; $C_{1-10}$ alkoxy; halosubstituted $C_{1-10}$ alkoxy; azide; $(CR_8R_8)q\ S(O)_tR_4$; hydroxy; hydroxy$C_{1-4}$alkyl; aryl; aryl $C_{1-4}$ alkyl; aryloxy; aryl$C_{1-4}$ alkyloxy; heteroaryl; heteroarylalkyl; heteroaryl $C_{1-4}$ alkyloxy; heterocyclic, heterocyclic $C_{1-4}$alkyl; aryl $C_{2-10}$ alkenyl; heteroaryl $C_{2-10}$ alkenyl; heterocyclic $C_{2-10}$ alkenyl; $(CR_8R_8)q\ NR_4R_5$; $C_{2-10}$ alkenyl $C(O)NR_4R_5$; $(CR_8R_8)q\ C(O)NR_4R_5$; $(CR_8R_8)q\ C(O)NR_4R_{11}$; $S(O)_3H$; $S(O)_3R_8$; $(CR_8R_8)q\ C(O)R_{11}$; $C_{2-10}$ alkenyl $C(O)R_{11}$; $C_{2-10}$ alkenyl $C(O)OR_{11}$; $(CR_8R_8)q\ C(O)OR_{12}$; $(CR_8R_8)q\ OC(O)\ R_{11}$; $(CR_8R_8)q\ NR_4C(O)R_{11}$, $(CR_8R_8)q\ NHS(O)_2R_d$, $(CR_8R_8)q\ S(O)_2NR_4R_5$ or two Y moieties together may form $O-(CH_2)_sO-$ or a 5 to 6 membered saturated or unsaturated ring; wherein the aryl, heteroaryl, heterocyclic containing moieties may be optionally substituted as defined herein.

When Y forms a dioxybridge, s is preferably 1. When Y forms an additional saturated or unsaturated ring, it is preferably 6 membered ring resulting in a naphthylene ring system. This naphthylene ring may be substituted 1 to 3 times by other Y moieties as defined above. The aryl, arylalkyl, arylalkenyl, heteroaryl, heteroarylalkyl, heteroarylalkenyl, heterocyclic, heterocyclicalkyl, and heterocyclicalkenyl moieties noted above may all be optionally substituted as defined herein.

Suitably, $R_d$ is a $NR_6R_7$, alkyl, aryl $C_{1-4}$ alklyl, aryl$C_{2-4}$ alkenyl, heteroaryl, hetroaryl-$C_{1-4}$alkyl, heteroaryl$C_{2-4}$ alkenyl, heterocyclic, heterocyclic$C_{1-4}$ alkyl, or heterocyclic $C_{2-4}$ alkenyl moiety, wherein the aryl, arylalkyl, arylalkenyl, heteroaryl, heteroarylalkyl, heteroarylalkenyl, heterocyclic, and heterocyclicalkyl, and heterocyclicalkenyl moieties noted above may all be optionally substituted as defined herein.

Y is preferably a halogen, $C_{1-4}$ alkoxy, optionally substituted aryl, optionally substituted aryloxy or arylalkoxy, methylene dioxy, $NR_4R_5$, thio $C_{1-4}$alkyl, thioaryl, halosubstituted alkoxy, optionally substituted $C_{1-4}$ alkyl, or hydroxy alkyl. Y is more preferably mono-substituted halogen, disubstituted halogen, mono-substituted alkoxy, disubstituted alkoxy, methylenedioxy, aryl, or alkyl, more preferably these groups are mono or di-substituted in the 2'-position or 2'-, 3'-position.

While Y may be substituted in any of the 5 ring positions Y is preferably mono-substituted in the 2'-position or 3'-position, with the 4'-preferably being unsubstituted; more preferably R is OH, SH, or $NSO_2R_b$. If the ring is disubstituted, preferably when R is OH, SH, or $NSO_2R_b$, then the substituents are preferably in the 2' or 3' position of a monocyclic ring. While both $R_1$ and Y can both be hydrogen, it is prefered that at least one of the rings be substituted, preferably both rings are substituted.

Preferably when Z is cyano, W is phenyl, R is OH, v is 0, and $W_1$ is a phenyl, than $(Y)_n$, wherein n is 1 or 2, is not mono substituted in the 3' position or di-substituted in the 3'–5' position of the phenyl ring with halogen, trifluromethyl, $OCF_3$, $C(O)_2H$, $C(O)_2$alkyl, $C(O)_2$aryl, $C(O)$ amino, CN, alkyl, alkoxy, hydroxy, nitro, hydroxymethyl, sulphamoyl, amino, aryloxy, alkylcarbonyl, arylcarbonyl, alkylcarbonyloxy, or arylcarbonyloxy.

Further, it is preferable that when Z is cyano, v is 0, W is phenyl, R is OH, $W_1$ is phenyl, then Y(n), where n is 1, is other than a 2-substituted arylalkyl, or arylalkenyl moiety (optionally substituted by alkyl).

In compounds of Formula (I), Z is suitably cyano, $OR_{11}$, $C(O)NR_{15}R_{16}$, $R_{18}$, $C(O)R_{11}$, $C(O)OR_{11}$, or $S(O)_2R_{17}$.

Suitably $R_{15}$ and $R_{16}$ are independently hydrogen, optionally substituted $C_{1-4}$ alkyl, optionally substituted aryl, optionally substituted aryl $C_{1-4}$alkyl, optionally substituted heteroaryl, optionally substituted heteroaryl$C_{1-4}$alkyl, optionally substituted heterocyclic, optionally substituted heterocyclic$C_{1-4}$alkyl, or $R_{15}$ and $R_{16}$ may together with the nitrogen to which they are attached form a 5 to 7 member ring optionally containing an additional heteroatom selected from oxygen, nitrogen, or sulfur.

Suitably, $R_{17}$ is $C_{1-4}$ alkyl, $NR_{15}R_{16}$, $OR_{11}$, optionally substituted aryl, optionally substituted aryl $C_{1-4}$alkyl, optionally substituted heteroaryl, optionally substituted heteroaryl$C_{1-4}$alkyl, optionally substituted heterocyclic, or optionally substituted heterocyclic$C_{1-4}$alkyl.

Suitably, $R_{18}$ is optionally substituted $C_{1-4}$ alkyl, optionally substituted aryl, optionally substituted aryl $C_{1-4}$alkyl, optionally substituted heteroaryl, optionally substituted heteroaryl$C_{1-4}$alkyl, optionally substituted heterocyclic, or optionally substituted heterocyclic$C_{1-4}$alkyl.

As used herein, "optionally substituted" unless specifically defined shall mean such groups as halogen, such as fluorine, chlorine, bromine or iodine; hydroxy; hydroxy substituted $C_{1-10}$ alkyl; $C_{1-10}$ alkoxy, such as methoxy or ethoxy; $S(O)_{m'}$ $C_{1-10}$ alkyl, wherein m' is 0, 1 or 2, such as methyl thio, methyl sulfinyl or methyl sulfonyl; amino, mono & di-substituted amino, such as in the $NR_4R_5$ group; $NHC(O)R_4$; $C(O)NR_4R_5$; $C(O)OH$; $S(O)_2NR_4R_5$; $NHS(O)_2R_{21}$, $C_{1-10}$ alkyl, such as methyl, ethyl, propyl, isopropyl, or t-butyl; halosubstituted $C_{1-10}$ alkyl, such $CF_3$; an optionally substituted aryl, such as phenyl, or an optionally substituted arylalkyl, such as benzyl or phenethyl, optionally substituted heterocylic, optionally substituted heterocylicalkyl, optionally substituted heteroaryl, optionally substituted heteroaryl alkyl, wherein these aryl, hetroaryl, or heterocyclic moieties may be substituted one to two times by halogen; hydroxy; hydroxy substituted alkyl; $C_{1-10}$ alkoxy; $S(O)m'C_{1-10}$ alkyl; amino, mono & di-substituted amino, such as in the $NR_4R_5$ group; $C_{1-10}$ alkyl, or halosubstituted $C_{1-10}$ alkyl, such as $CF_3$.

$R_{21}$ is suitably $C_{1-4}$ alkyl, aryl, aryl $C_{1-4}$alkyl, heteroaryl, heteroaryl$C_{1-4}$alkyl, heterocyclic, or heterocyclic$C_{1-4}$alkyl.

Suitable pharmaceutically acceptable salts are well known to those skilled in the art and include basic salts of inorganic and organic acids, such as hydrochloric acid, hydrobromic acid, sulphuric acid, phosphoric acid, methane sulphonic acid, ethane sulphonic acid, acetic acid, malic acid, tartaric acid, citric acid, lactic acid, oxalic acid, succinic acid, fumaric acid, maleic acid, benzoic acid, salicylic acid, phenylacetic acid and mandelic acid. In addition, pharmaceutically acceptable salts of compounds of Formula (I) may also be formed with a pharmaceutically acceptable cation, for instance, if a substituent group comprises a carboxy moiety. Suitable pharmaceutically acceptable cations are well known to those skilled in the art and include alkaline, alkaline earth, ammonium and quaternary ammonium cations.

The following terms, as used herein, refer to:

"halo"—all halogens, that is chloro, fluoro, bromo and iodo.

"$C_{1-10}$alkyl" or "alkyl"—both straight and branched chain radicals of 1 to 10 carbon atoms, unless the chain length is otherwise limited, including, but not limited to, methyl, ethyl, n-propyl, iso-propyl, n-butyl, sec-butyl, iso-butyl, tert-butyl, n-pentyl and the like.

The term "cycloalkyl" is used herein to mean cyclic radicals, preferably of 3 to 8 carbons, including but not limited to cyclopropyl, cyclopentyl, cyclohexyl, and the like.

The term "alkenyl" is used herein at all occurrences to mean straight or branched chain radical of 2–10 carbon atoms, unless the chain length is limited thereto, including, but not limited to ethenyl, 1-propenyl, 2-propenyl, 2-methyl-1-propenyl, 1-butenyl, 2-butenyl and the like.

"aryl"—phenyl and naphthyl;

"heteroaryl" (on its own or in any combination, such as "heteroaryloxy", or "heteroaryl alkyl")—a 5–10 membered aromatic ring system in which one or more rings contain one or more heteroatoms selected from the group consisting of N, O or S, such as, but not limited, to pyrrole, pyrazole, furan, thiophene, quinoline, isoquinoline, quinazolinyl, pyridine, pyrimidine, oxazole, thiazole, thiadiazole, triazole, imidazole, or benzimidazole.

"heterocyclic" (on its own or in any combination, such as "heterocyclicalkyl") —a saturated or partially unsaturated 4–10 membered ring system in which one or more rings contain one or more heteroatoms selected from the group consisting of N, O, or S; such as, but not limited to, pyrrolidine, piperidine, piperazine, morpholine, tetrahydropyran, or imidazolidine.

The term "arylalkyl" or "heteroarylalkyl" or "heterocyclicalkyl" is used herein to mean $C_{1-10}$ alkyl, as defined above, attached to an aryl, heteroaryl or heterocyclic moiety, as also defined herein, unless otherwise indicated.

"sulfinyl"—the oxide S (O) of the corresponding sulfide, the term "thio" refers to the sulfide, and the term "sulfonyl" refers to the fully oxidized $S(O)_2$ moiety.

The term "wherein two $R_1$ moieties (or two Y moieties) may together form a 5 or 6 membered saturated or unsaturated ring" is used herein to mean the formation of a napthylene ring system or a phenyl moiety having attached a 6 membered partially unsaturated ring such as a $C_6$ cycloalkenyl, i.e hexene, or a $C_5$ cyloalkenyl moiety, cyclopentene.

Exemplified compounds of Formula (I) include:

N-(2-Hydroxy-4-nitrophenyl)-N'-(2-chlorophenyl)-N"-cyanoguanidine

N-(2-Hydroxy 4-nitro phenyl) N'-(2-chloro phenyl)-N"-cyanoguanidine

N-(4—Cyano-2-hydroxyphenyl)-N'-(phenyl)cyanoguanidine

N-(2-Bromophenyl) N'-(4-cyano-2-hydroxyphenyl) N"-cyanoguanidine

N-(4-Cyano-2-hydroxyphenyl)-N'-(2,3-dichlorophenyl)-N"-cyanoguanidine

N-(2-Bromophenyl)-N'-(4-cyano-2-hydroxy-3-propylphenyl)-N"-cyanoguanidine

N-(2-Bromophenyl)-N'-(4-cyano-2-hydroxy-3-isobutylphenyl)-N"-cyanoguanidine

N-(2-Bromophenyl)-N'-(3-bromo-4-cyano-2-hydroxyphenyl)-N"-cyanoguanidine

N-(4-Cyano-2-hydroxy-3-propylphenyl)-N'-(2,3-dichlorophenyl)-N"-cyanoguanidine

N-(3-Bromo-4-cyano-2-hydroxyphenyl)-N'-(2,3-methylenedioxyphenyl)-N"-cyanoguanidine N-(2-Chlorophenyl)-N'-(4-cyano-2-hydroxy-3-propylphenyl)-N"-cyanoguanidine N-(2-Bromophenyl)-N'-(4-cyano-2-hydroxy-3-methoxycarbonylphenyl)-N"-cyanoguanidine It is recognized that the compounds of the present invention may exist as stereoisomers, regioisomers, or diastereiomers. These compounds may contain one or more asymmetric carbon atoms and may exist in racemic and optically active forms. All of these compounds are included within the scope of the present invention.

The compounds of Formula (I) may be obtained by applying synthetic procedures, some of which are illustrated in the Schemes below. The synthesis provided for in these Schemes is applicable for the producing compounds of Formula (I) having a variety of different R, $R_1$, and Aryl groups which are reacted, employing optional substituents which are suitably protected, to achieve compatibility with the reactions outlined herein. Subsequent deprotection, in those cases, then affords compounds of the nature generally disclosed. Once the urea nucleus has been established, further compounds of these formulas may be prepared by applying standard techniques for functional group interconversion, well known in the art. While the schemes are shown with compounds only of Formula (I) this is merely for illustration purposes only.

Methods of Preparation

The title compounds can be synthesized from the thiouronium salt (2, Scheme 1). R' represents the —$(R_{13}R_{14})_v$—$W_1$ linkage as defined in compounds of Formula (I). For purposes of illustration herein the schemes represent the W term by a substituted phenyl.

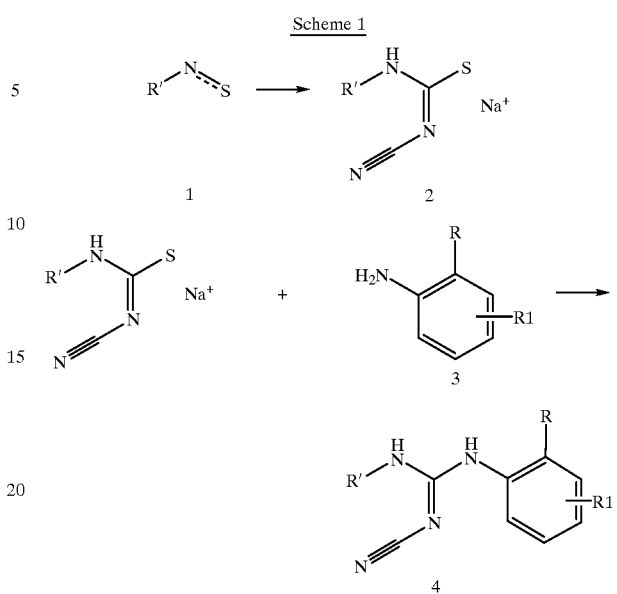

a) Na, EtOH, cyanamide b) EDC·HCl

The thiouronium salt(2, Scheme 1) can be synthesized by reacting sodium cyanamide with a commercially available isothiocyanate 1 (if the isothiocyanate is not commercially available it can be synthesized by reacting the desired amine with thiophosgene in the presence of a base like sodium bicarbonate). The thiouronium salt (2) can then be condensed with the appropriate substituted aniline in the presence of a coupling reagent like EDC.HCl or acidified to form the cyanothiourea and then reacted.

Alternatively 4 can be synthesized by reacting the commercially available (Aldrich Chem. Co.), diphenyl cyanocarboimidate (5, Scheme 2) with an amine to form an intermediate O-phenylisourea 6 which then reacts with the appropriately substituted aniline in the presence of trimethyl aluminum by the method of Atwal. (Atwal, K. S., Tetrahedron Lett, 35, 8085 (1994).). Compounds wherein R' is alkyl may be prepared by heating with the appropriately substituted alkylamine, but without the presence of catalyst.

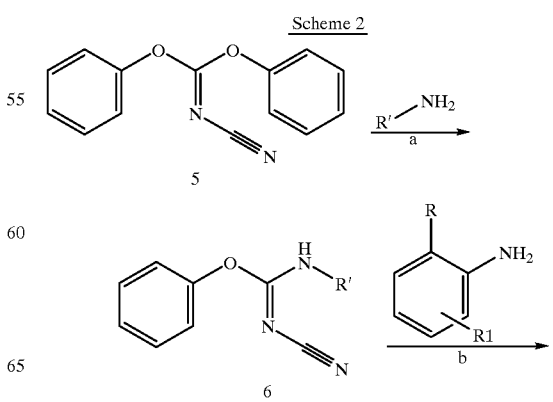

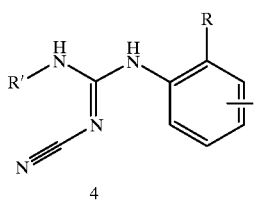

a) acetonitrile; heat b) AlMe₃

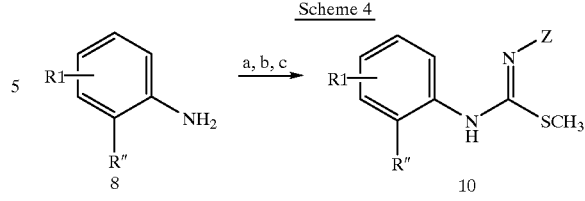

a) ClCSCl, NaHCO₃ b) ZNH⁻ c) MeI

Alternatively the title compound can be synthesized using a protected ortho-substituted aniline (8, Scheme 3, See synthesis as described in US provisional application U.S. Ser. No. 60/020655 filed Jun. 27, 1996, Attorney Docket No.: P50467P; WO96/25 157 filed Aug. 22, 1996, Widdowson et al. (Attorney Docket No.: P50324-1); and U.S. Ser. No. 08/701,299 filed Aug. 21, 1996 (Attorney Docket No.: P50324-2) whose disclosures are incorporated herein by reference in their entireties. An ortho-substituted aniline (7, Scheme 3) is first protected (ie. tert-butyl dimethyl silyl, allyl, benzyl, mom or other suitable protecting group) by reacting the ortho-substituted aniline with the appropriate alkyl or silyl halide in the presence of a suitable base (ie. cesium carbonate, potassium carbonate or imidazole) in an aprotic solvent. The protected ortho-substituted aniline may also be synthesized from an ortho-substituted nitrobenzene (9) by reacting it with a protecting group under conditions well known in the art (see Greene, T *Protecting, Groups in Organic Synthesis*, Wiley&Sons, New York, 1981) This protected ortho-substituted nitro compound is then reduced to the corresponding aniline using SnCl₂ in EtOH or alternately H₂/Pd or LiAlH₄ in an aprotic solvent.

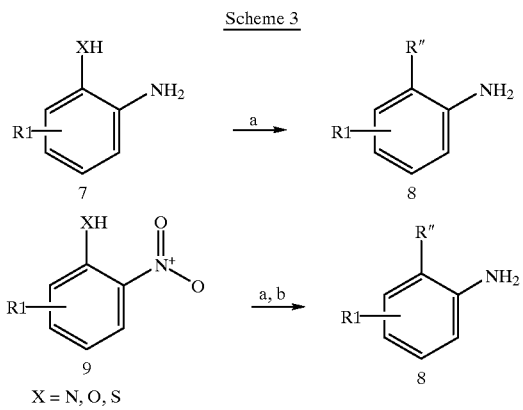

X = N, O, S a) Alkyl or silyl halide, base b) reducing agent

This protected ortho-substituted aniline (8) can then be converted into an isothiocyanate using thiophosgene and then reacted with the anion ZNH⁻ (formed from reaction of ZNH₂ with a base such as NaH). Z is as defined in compounds of Formula (I).The resulting thioanion can then be alkylated with an alkylating agent like methyl iodide to form a thioimidate such as 10 (Scheme 4).

The thioimidate (10, Scheme 5) can be converted to the title compound 4 by reaction with the amine R'NH₂. This reaction can be accelerated by the addition of metal salt with a high affinity for sulfur such as mercuric oxide or silver acetate or by oxidation of the sulfur with dimethyloxirane to form a better leaving group. Finally the phenol protection is removed by standard methods to form the title compound 4.

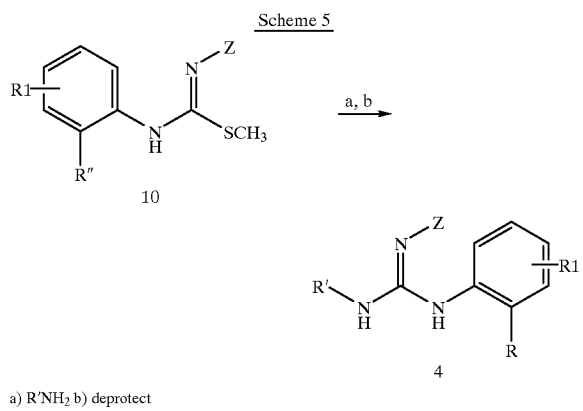

a) R'NH₂ b) deprotect

Alternately the title compound could be synthesized by reaction of a protected carbodiimide (11, Scheme 6) with the anion NH—Z (formed from reaction of NH₂Z with a base such as NaH) or the neutral species NH₂Z (Z=CN) and a tertiary amine base, such as Hunig's base (diisopropylethylamine), triethylamine, triisopropylethylamine, N,N-dimethylbenzylamine, or N,N-dimethylisopropylamine, under conditions where the nucleophile is present in large excess and the reaction time is kept as short as possible by carefully monitoring the reaction for completion followed by deprotection. Other suitable bases for use herein include, secondary amine, such as pyridine, and amino substituted pyridine derivatives. Suitable solvents for use herein when Z is cyano include various aprotic solvents, such as acetonitrile; halogenated solvents, such as chloroform and methylene chloride; ethyl gylcol-dimethyl ether (monoGLYME), dioxane, DMF and DMSO; or mixtures thereof, preferably acetonitrile. It is recognized by the skilled artisan that the limiting feature fo use of solvents herein will be the solubility of the cyano derivatived compound. For compounds wherein Z is other than cyano, while aprotic solvents are prefered, it is recognized by the skilled artisan that other suitable solvents, such as protic solvents, i.e. alcohols, may be used.

Preferably the reaction (when Z is cyano) temperature is from about −10° to about 100°, preferably about 10° to about 50°, more preferably around room temperature, i.e. 20 to 30° C.

The protected R" moiety may be suitably deprotected using art recognized techniques. Preferably the deprotection is by deallylation catalyzed by palladium (O) when the protecting group is an allyl derivative.

Scheme 6

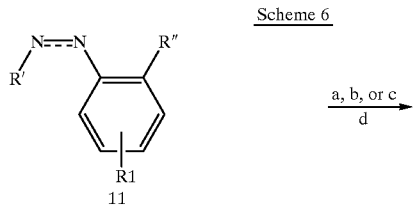

11

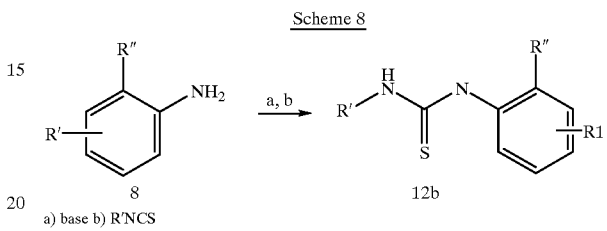

a) ZNH⁻(ZNH² + NaH) for Z = OR, COOEt, CHO, RNHSO₂, ArNHSO₂;
b) ZNH₂•HCl for Z = OH c) ZNH2 and NR3 for Z = CN d) deprotect The carbodiimide 11 is prepared from the thiourea (12a, Scheme 7) by treatment with phosgene and a tertiary amine base or from the thiourea (12a) or urea (12b) by reaction with triphenylphosphine, carbon tetrachloride and triethylamine.

The carbodiimide may also be prepared by reaction of the thiourea (12b) with an excess, such as 2 or more equivalents of methanesulfonyl chloride and a tertiary amine base, such as Hünig's base (diisopropylethylamine), triethylamine, triisopropylethylamine, N,N-dimethylbenzylamine, or N,N-dimethylisopropylamine, preferably triethylamine. The reaction may use any halogenated solvent, such as methylene chloride, chloroform, or tetrachloroethylene, etc.; suitable reaction temperatures are from about −30° C. to about 80° C., preferably −10° C. to about 50° C., more preferably from about 0° C. to about room temperature. See Fell and Coppola (Fell, J. B., Coppola, J. B., Syn Communications 25, 43, (1995).

Scheme 7

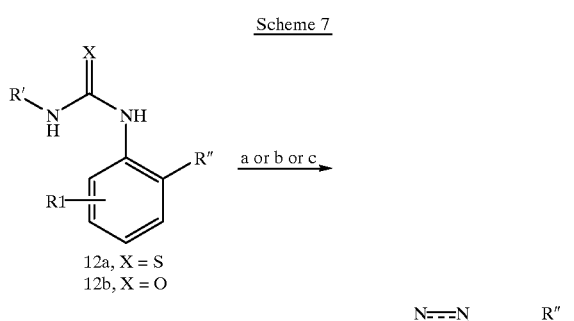

12a, X = S
12b, X = O

a) phosgene, Et₃N, b) Ph₃P, CCl₄, Et₃N; c) MsCl, Et₃N

The thiourea or urea is synthesized as described in the US provisional application U.S. Ser. No. 60/020655 filed Jun. 27, 1996, Attorney Docket No.: P50467P and Attorney Docket No.: P50324-2, whose disclosure is incorporated herein by reference. The thiourea (12a, Scheme 8) may also be prepared by reaction of the protected ortho-substituted aniline and two equivalents of an appropriate base such as NaH, KH, calcium hydride, and reacting this anion with a commercially available isothiocyanate ($W_1$—NCS, wherein $W_1$ is as defined for compounds of Formula (I)). The reaction make take place in any suitable aprotic solvent or halogenated solvent, preferably dimethyl formamide. Suitable reaction temperatures for this reaction are from about −10° to about 50°.

If the desired isothiocyanate is not commercially available, it may be prepared by reaction of a corresponding aniline with thiophosgene and a suitable base such as sodium bicarbonate.

Scheme 8

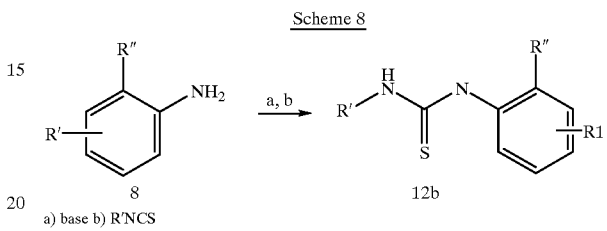

8                                    12b a) base b) R'NCS

Another aspect of the present invention are the novel compounds of Formula (II)

$$W_1-N=C=N-W \quad \text{(II)}$$

wherein W, and $W^1$ are as defined for formula (I), and W contains a protected or unprotected R group (R") as defined for compounds of Formula (I).

Another aspect of the present invention are the novel compounds of Formula (III)

$$W_1-NH-C(S)-NH-W \quad \text{(III)}$$

wherein W, and $W^1$ are as defined for formula (I), and W contains a protected or unprotected R group (R") as defined for compounds of Formula (I).

Also, the protected (R") versions of compounds of Formula (I) are contemplated as being within the scope of this invention.

It is recognized that the guanidine functionality may hve a number of different tautomers, such as $W_1$—N—C(=NZ)—NW; ZN=C($NW_1$)—NW; $W_1$—N—C(=NW)—NZ, all of which are within the scope of this invention.

Pharmaceutically acceptable salts of compounds of Formula (I) may be obtained in known manner, for example by treatment thereof with an appropriate amount of acid or base in the presence of a suitable solvent.

In the Examples, all temperatures are in degrees Centigrade (° C.). Mass spectra were performed upon a VG Zab mass spectrometer using fast atom bombardment, unless otherwise indicated. ¹H-NMR (hereinafter "NMR") spectra were recorded at 250 MHz or 400 MHz using a Bruker AM 250 or AM 400 spectrometer, respectively. Multiplicities indicated are: s=singlet, d=doublet, t=triplet, q=quartet, m=multiplet and br indicates a broad signal. Sat. indicates a saturated solution, equiv. indicates the proportion of a molar equivalent of reagent relative to the principal reactant.

Flash chromatography is run over Merck Silica gel 60 (230–400 mesh).

SYNTHETIC EXAMPLES

The invention will now be described by reference to the following examples which are merely illustrative and are not to be construed as a limitation of the scope of the present invention. All temperatures are given in degrees centigrade, all solvents used herein are of the highest available purity and all reactions are run under anhydrous conditions in an argon atmosphere unless otherwise indicated.

Example 1

Preparation of N-(2-Hydroxy-4-nitrophenyl)-N'-(2-chlorophenyl)-N"-cyanoguanidine.

a) Sodium salt of N-(2-chlorophenyl)-N"-cyanothiourea

Sodium (1.64 g, 71.3 mmol) was dissolved in ethanol until all gas evolution had ceased. Then cyanamide (1.685 g, 40 mmol) was added. The reaction mixture was stirred for 15 min, 2-chlorophenylisothiocyanate (7.21 g, 42.66) was added and the mixture kept at reflux for 6 hr. The reaction was cooled and diluted with methylene chloride. A white solid precipitated which was filtered and dried to give the sodium salt of N-(2-chlorophenyl)-N"-cyanothiourea. ( 8.26 g, 87.5%). MS(ES$^+$) m/e 210,212 [M+H]$^+$ b) N-(2-Hydroxy-3-nitrophenyl)-N'-(2-chlorophenyl)-N"-cyanoguanidine To a stirred solution of the sodium salt of N-(2-chlorophenyl)-N'-cyanothiourea (234 mg, 1 mmol) and 2-hydroxy-3-nitro-aniline(156 mg, 1 mmol) in 2 ml dry DMF was added EDC hydrochloride (384 mg, 2 mmol) under Ar and the reaction stirred at rt for 4 d. The reaction mixture was partitioned between EtOAc and 1 N HCl and the organic extracts were washed with water and brine. After drying (Na$_2$SO$_4$) and evaporation of the solvent under reduced pressure, a red oil was isolated. Chromatography (silica gel, 3% acetone/CHCl$_3$) afforded a bright yellow solid.(30 mg, 9%) which was recrystallized from t-butylmethylether to afford the title compound. $^1$H NMR(400 MHz, CDCl$_3$) δ 10.93 (s, 1H), 8.53 (s, 1H), 7.92 (d, J=7.8 Hz, 1H),7.61 (d, J=7.8 Hz, 2H), 7.38–7-50 (m, 2H), 7.22 (s, 1H), 7.08 (t, 1H); IR(KBr) 2181 cm$^{-1}$; MS(ES$^-$) m/e 330[M–H]$^-$; mp. 163–164°.

Example 2

Preparation of N-(2-Hydroxy-4-cyanophenyl)-N'-(2-bromophenyl)-N"-cyanoguanidine.

a) 1-Allyloxy-5-cyano-2-nitrobenzene

A mixture of 5-cyano-2-nitro-phenol (3.0 g, 18.9 mmol), allyl bromide (1.82 ml, 21.0 mmol) and cesium carbonate (7.39 g, 22.7 mmol) in DMF (20 ml) was stirred at rt for 18 hrs under Ar. The reaction mixture was partitioned between t-butyl-methylether and water. The layers were separated and the aqueous portion was further extracted (×3). The combined organic extracts were washed twice with water, then brine and dried over MgSO$_4$ and filtered. Removal of solvent at reduced pressure afforded the title compound (3.89 g, 100%). $^1$H NMR(400 MHz, CDCl$_3$) δ 7.87 (d, J=8.5 Hz, 1H), 7.35 (dd, J=8.4 Hz J=1.2 Hz 1H), 7.35 (d, J=1.5 Hz, 1H), 6.02 (m, 1H), 5.52 (d, 1H), 5.43 (d, 1H), 4.73 (dd, J=3.6 Hz J=1.2 Hz 2H);

b) 2-Allyloxy-4-cyanoaniline

A mixture of 1-allyloxy-5-cyano-2-nitrobenzene (3.6 g, 17.46 mmol) and tin (II) chloride (19.7 g, 87.3 mmol) in ethanol (100 ml) was stirred overnight at rt. The solvent was removed under reduced pressure. The reaction mixture was partitioned between 5% NaHCO$_3$ and ethyl acetate. The mixture was filtered to remove the tin salts and the aqueous was further extracted with ethyl acetate (×4). The combined organic phases were washed with water and brine, dried over MgSO$_4$ Removal of solvent at reduced pressure gave a brown solid (2.82 g) which was recrystallized from t-butylmethylether/hexane to give the title compound as a pale brown solid. (2.63 g, 93%) MS(ES+) m/e 175 [M+H]+; MS(ES$^-$) m/e 173 [M–H]$^-$;

c) N-(2-Allyloxy-4-cyanophenyl)-N'-(2-bromophenyl)-thiourea.

To sodium hydride (60% oil dispersion, 240 mg, 6.0 mmol), previously washed with hexanes, in DMF (10 ml) was added at 0° 2-allyloxy-4-cyanoaniline (522 mg, 3 mmol) in DMF (1.5 ml). After stirring for 15 minutes at 0° C. under Ar, 2-bromophenyl isothiocyanate was added dropwise at 0° and the reaction was stirred for 1 hr at room temperature. The reaction was quenched by addition of 0.5 M sodium dihydrogen phosphate. The mixture was extracted with ethyl acetate, washed with water and dried over sodium sulfate. The crude solid was recrystallized from methanol to give the title compound as a white solid (911 mg, 78%) MS(ES$^+$) m/e 388, 390 [M+H]$^+$ d) N-(2-Allyloxy-4-cyanophenyl)-N'-(2-bromophenyl)-carbodiimide To a stirred solution of N-(2-Allyloxy-4-cyanophenyl)-N'-(2-bromophenyl)-thiourea (900 mg, 2.32 mmol) and triethylamine (1 ml, 6.95 mmol) in methylene chloride was added dropwise at 0° methanesulfonyl chloride (360 μL, 4.64 mmol) under Ar. The reaction was stirred for 15 minutes at 0° and tlc showed no starting material present. The reaction mixture was chromatographed on silica gel eluting with methylene chloride to afford the title compound as a yellow solid (1.2 g, >100%). This was used in the next reaction without further purification.

e) N-(2-Allyloxy-4-cyanophenyl)-N'-(2-bromophenyl)-N"-cyanoguanidine.

To a stirred mixture of cyanamide (560 mg, 13.33 mmol) and Huinig's base (2.6 ml) in acetonitrile was added a solution of N-(2-Allyloxy-4-cyanophenyl)-N'-(2-bromophenyl)-carbodiimide (600 mg, 1.69 mmol) in acetonitrile (30 ml) dropwise. The reaction was stirred at rt for 15 min, then the solvent was removed under reduced pressure and the residue hydrolyzed with 0.5 M sodium dihydrogen phosphate. Ethyl acetate extractions of the aqueous mixture were washed with 0.5 M sodium dihydrogen phosphate and brine. After drying (MgSO$_4$) filtration and evaporation under reduced pressure afforded a crude tan solid (500 mg). This was chromatographed on silica gel (50/50 ethyl acetate/hexane) to give the title compound (455 mg, 95%). MS(ES$^-$) m/e 394, 396 [M–H]$^-$ f) N-( 4-Cyano-2-hydroxyphenyl)-N'-(2-bromophenyl)-N"-cyanoguanidine.

To a mixture of N-(2-Allyloxy-4-cyanophenyl)-N'-(2-bromophenyl)-N"-cyanoguanidine (100 mg, 0.25 mmol) and sodium borohydride (20 mg, 0.52 mmol) in THF (3 ml) was added at rt tetrakistriphenylphosphine palladium[0] (21 mg, 7 mol %). The reaction was stirred at rt until tlc showed no starting material present. The mixture was partitioned between ethyl acetate and 0.5 M sodium dihydrogen phosphate. After drying over MgSO$_4$ filtration and evaporation under reduced pressure afforded a crude tan solid (100 mg). Column chromatography on silica gel eluting with 5% methanol/chloroform gave the title compound as a pale yellow solid (64 mg) which was recrystallized from chloroform (42 mg, 47%). $^1$H NMR(400 MHz,DMSO) δ 10.93 (s, 1H), 9.57 (s, 1H), 8.74(s, 1H), 7.84 (d, J=8.3 Hz, 1H),7.71 (d, J=7.8 Hz, 2H), 7–50–7.42 (m, 2H), 7–30–7.26 (m, 2H 7.17 (s, 1H), 7.08 (t, 1H); IR(KBr) 2224,2193 cm$^{-1}$; MS(ES$^-$) m/e 354,356 [M–H]$^-$; MS(ES$^+$) m/e 356,358 [M+H]$^+$; mp. 175–176°.

Example 3

Preparation of N-(4-Cyano-2-hydroxyphenyl)-N'-(phenyl) -N"-cyanoguanidine a) 5-Cyano-1-methoxymethyloxy-2-nitrobenzene To sodium hydride (60% oil dispersion, 260 mg, 6.5 mmol), previously washed with hexanes, in THF (5 ml) was added dropwise at rt 5-cyano-2-nitro-phenol (978 mg, 5.96 mmol) in THF (10 ml). The solution turned bright orange and a large prepipitate formed. After stirring 15 min at rt bromomethylmethylether was added dropwise to this stirred slurry and the reaction was stirred for 18 h at rt. The yellow-colored mixture was then partitioned between t-butyl-O-methylether and water and the aqueous portion was extracted (×3) and washed with 5% sodium bicarbonate solution (×4) and brine. After drying (MgSO$_4$), filtration and evaporation under reduced pressure afforded the title compound as a pale yellow solid (1.05 g, 85%). $^1$H NMR(400 MHz, CDCl$_3$) δ 7.84 (d, J=8.4 Hz, 1H), 7.66 (d, J=1.4 Hz 1H), 7.35 (dd, J=8.4 Hz J=1.5 Hz, 1H), 5.34 (s, 2H), 3.55 (s, 3H).

b) 4-Cyano-2-methoxymethyloxyaniline

A mixture of 5-cyano- 1 -methoxymethyloxy-2-nitrobenzene (0.5 g, 2.4 mmol) and 10% palladium on carbon (.05 g) in ethyl acetate (50 mL) was stirred at rt under 1 atm of hydrogen for 72 h. The mixture was filtered through Celite to remove the palladium and the residue was chromatographed on silica gel (eluting with 25% ethylacetate/hexane) to afford the title compound (250 mg, 58%). MS(ES$^+$) m/e 179 [M+H]$^+$ c) N-(4-cyano-2-methoxymethyloxyphenyl)-N'-(2-phenyl)-N"-cyanoguanidine Following the procedure of Example 1(c)–1(e), except substituting phenylisothiocyanate for 2-bromophenylisothiocyanate and substituting 2-methoxymethyloxy-4-cyanoaniline for 2-allyloxy-4-cyanoaniline, the title compound was prepared (24% overall). IR(KBr) 2226, 2198 cm$^{-1}$; MS(ES$^-$) m/e 320 [M–H]$^-$ d) N-(4-Cyano-2-hydroxyphenyl)-N'-(phenyl) -N"-cyanoguanidine The compound of Example 2(b) (47 mg, 0.146 mmol) was dissolved in ethyl acetate (20 mL), treated with 6 N HCl (10 mL) and stirred at rt for 3 h . Then 6 N HCl (5 mL) was added and stirring continued for 2 more h. The mixture was diluted with ethyl acetate and brine and the aqueous portion extracted further with ethyl acetate (×5). The combined organic portions were dried over sodium sulfate and evaporated in vacuo to give the title compound (64 mg) which was recrystallized from t-butyl-O-methylether to give the title compound as a white solid (2 mg, 5%). $^1$H NMR(400 MHz, DMSO d$_6$) δ 9.70 (s, 1H), 9.12 (s, 1H), 7.62 (d, J=8.3 Hz, 1H), 7.55 (d, J=1.2 Hz, 1H), 7.49 (dd, J=1.2 Hz, J=8.1 Hz, H), 7.36 (m, 4H), 7.18 (m, 1H); IR(KBr) 2233,2192 cm$^{-1}$; MS(ES$^+$) m/e 278 [M+H]$^+$; MS(ES$^{--}$) m/e 276 [M–H]$^-$; mp 270–271° C.

Example 4

Preparation of N-(4-cyano-2-hydroxyphenyl)-N'-(2.3-dichlorophenyl)-N"-cyanoguanidine Following the procedure of Example 1 (a)–1(e), except substituting (2,3-dichlorophenylisothiocyanate for 2-bromophenylisothiocyanate, the title compound was prepared (17% overall). IR(KBr) 2231, 2197 cm$^{-1}$; MS(ES$^+$) m/e 346, 348, 350 [M+H]$^+$; MS(ES$^-$) m/e 344, 346, 347, 348 [M–H]$^-$; mp 155–156° C.

Example 5

Preparation of N-(2-bromophenvl)-N'-(4-cyano-2-hydroxy-3-propylphenyl)-N"-cyanoguanidine a) 2-Amino-5-cyano-6-prop-1-ene-3-yl-phenol The compound prepared in Example 2(b) (1.88 g, 1.29 mmol) was treated with N,N-dimethylaniline (20 mL) under Ar and was kept for 3.5 h at 175° (oil bath temperature). The solvent was removed in vacuo and the residue was recrystallized from methyl-t-butylether with 10–20% of each methylene chloride and hexane to afford the title compound as a clear solid (1.67 g, 89%). MS(ES$^+$) m/e 175 [M+H]$^+$; MS(ES$^-$) m/e 173 [M–H]$^-$;

b) 2-Amino-5-cyano-6-propyl-phenol

A mixture of 2-amino-5-cyano-6-prop-1-ene-3-yl-phenol (0.5 g, 2.4 mmol) and 10% palladium on carbon (0.05 g) in ethyl acetate (50 mL) was stirred at rt under 1 atm of hydrogen for 2 hours. The mixture was filtered through Celite to remove the palladium and the filtrate was concentrated under reduced pressure to afford the title compound as a pinkish-white solid (1.2 g, 78%). MS(ES$^+$) m/e 177 [M+H]$^+$; MS(ES$^-$) m/e 175[M–H]$^-$.

c) N-(2-bromophenyl)-N'-(4-cyano-2-hydroxy-3-propylphenyl)-N"-cyanoguanidine

Following the procedure of Example 2(a)–1(e), except substituting 2-Amino-5-cyano-6-propyl-phenol for 5-cyano-2-nitro-phenol, the title compound was prepared (37% overall). $^1$H NMR(400 MHz, DMSO d$_6$) δ 9.72 (s, 1H), 9.45 (s, 1H), 8.66 (s, 1H), 7.71 (d, J=7.0 Hz, 1H), 7.56 (d, J=8.4 Hz, 1H), 7.45 (m, 2H), 7.28 (d, J=8.4 Hz, 1H), 7.26 (t, 1H), 2.76 (t, J=7.5, 2H), 1.55 (hextet, J=7.6, 2H), 0.93(t, J=7.3, 3H); IR(KBr) 2224, 2184 cm$^{-1}$; MS(ES$^+$) m/e 398, 400 [M+H]$^+$; MS(ES$^-$) m/e396, 398 [M–H]$^-$;

Example 6

Preparation of N-(4-cyano-2-hydroxy-3-propylphenyl)-N'-(2.3-dichlorophenyl)-N"-cyanoguanidine Following the procedure of Example 1 (b)–1(e), except substituting 2,3-dichlorophenylisothiocyanate for 2-bromophenylisothiocyanate and substituting 2-Allyloxy-4-cyano-3-propylaniline for 2-allyloxy-4-cyanoaniline, the title compound was prepared (7% overall). IR(KBr) 2236, 2182 cm$^{-1}$; MS(ES$^+$) m/e 388,390,391 [M+H]$^+$; MS(ES$^-$) m/e 386,388,390 [M–H]$^-$; mp 143–147° C.

Example 7

Preparation of N-(2-chlorophenyl)-N'-(4-cyano-2-hydroxy-3-propylphenyl)-N"-cyanoguanidine Following the procedure of Example 1 (b)–1(e), except substituting 2-chlorophenylisothiocyanate for 2-bromophenylisothiocyanate and substituting 2-allyloxy-4-cyano-3-propylaniline for 2-allyloxy-4-cyanoaniline, the title compound was prepared (26% overall). IR(KBr) 2225, 2187 cm$^{-1}$; MS(ES$^+$) m/e 354, 356 [M+H]$^+$; MS(ES$^-$) m/e 352, 354 [M–H]$^-$; mp 159–160° C.

Example 8

Preparation of N-(2-bromophenyl)-N'-(-4-cyano-2-hydroxy-3-isobutyllphenyl)-N"-cyanoguanidine Following the procedure of Example 4(a)–1(c), except substituting 3-bromo-2-methyl-1-propene for allyl bromide, the title compound was prepared (16% overall).). IR(KBr) 2231, 2189 cm$^{-1}$; MS(ES$^+$) m/e 412, 414 [M+H]$^+$; MS(ES$^-$) m/e 410, 412 [M–H]$^-$;

Example 9

Preparation of N-(2-bromophenyl)-N'-(3-bromo-4-cyano-2-hydroxyvhenyl)-N"-cyanogiuanidine a) 2-Bromo-3-hydroxy-4-nitrobenzonitrile.

To a solution of 3-hydroxy-4-nitrobenzonitrile (3.03 g, 18.4 mmol)in methylene chloride (660 ml) hexamethylenetetraamine compound with hydrogen tribromide (1:1) (9.91 g, 26.0 mmol) was added. The resulting solution was allowed to stir for 1 week at rt. The reaction mixture was acidified with 1N HCl, and then extracted with a 1/1 mixture of EtOAc/hexane. The organic layers were combined, dried over $MgSO_4$, and filtered. The solvent was evaporated and chromatography of the resulting solid on silica gel (50/50: hexahel EtOAc) gave the desired product (1.47 g, 35.0%). $MS(ES^-)$ m/e 241,243 $[M-H]^-$.

b) N-(2-bromophenyl)-N'-(3-bromo-4-cyano-2-hydroxyphenyl)-N"-cyanoguanidine

Following the procedure of Example 2(a)–1(e), except substituting 2-bromo-3-hydroxy-4-nitrobenzonitrite for 5-cyano-2-nitro-phenol, the title compound was prepared as an off-white solid.(44% overall after chrom, 15% recrystallized ). $^1H$ NMR(400 MHz, DMSO $d_6$) δ 10.66 (s, 1H), 9.56 (s, 1H), 8.92 (s, 1H), 7.71 (d, J=8.0 Hz, 1H), 7.68 (d, J=8.5 Hz, 1H), 7.48-7.41 (m, 3H), 7.26 (t, 1H); IR(KBr) 2228, 2186cm$^{-1}$; $MS(ES^+)$ m/e 434,436,438 $[M+H]^+$; $MS(ES^-)$ m/e 432,434,436 $[M-H]^-$; mp 142° C.

Example 10

Preparation of N-(3-bromo-4-cyano-2-hydroxyphenyl)-N'-(2,3-methylenedioxyphenyl)-N"-cyanoguanidine Following the procedure of Example 8(a)–1(b), except substituting methylenedioxyphenylisothiocyanate for 2-bromophenylisocyanate the title compound was prepared (14% overall) IR(KBr) 2230, 2196cm$^{-1}$; $MS(ES^+)$ m/e 400, 402 $[M+H]^+$; $MS(ES^-)$ m/e 398,400$[M-H]^-$; mp 164–165° C.

Example 11

Preparation of N-(2-bromophenyl)-N'-(4-cyano-2-hydroxy-3-methoxycarbonylphenyl )-N"-cyanoguanidine a) Methyl-2,6-dihydroxybenzoate.

A solution of 80% NaH (10.00 g, 333.3 mmol) in DMF (45 mL) was chilled to 0° C. under Ar. To this mixture, 2,6-dihydroxybenzoic acid (48.88 g, 317.1 mmol) in DMF (50 mL) was added slowly over 45 min. The solution was allowed to stir for 45 min, then MeI (21.0 mL, 337 mmol) was added over 20 min. The resulting solution was allowed to stir at rt for 70 h. The mixture was diluted with methylene chloride, and filtered through a plug of silica gel using methylene chloride as a wash. The solvent was evaporated to give the desired product (35.22 g, 66.1%). $^1H$ NMR(250 MHz, DMSO $d_6$) δ 9.91 (s, 2H), 7.09 (t, J=1.2 Hz, J=2.5 Hz, 1H), 6.37 (d, J=1.1 Hz, 2H), 3.78 (s, 3H).

b) Methyl-2-benzyloxy-6-hydroxybenzoate.

To a mixture of methyl-2,6-dihydroxybenzoate (20.00 g, 118.9 mmol) in DMF (100 mL) under Ar, 80% NaH (3.9144 g, 130.5 mmol) is added, followed by the addition of benzylbromide (25.5 mL, 214.5 mmol). The solution was heated at 70° C. for 20 h. The mixture was cooled followed by addition of saturated sodium bicarbonate, extracted with EtOAc, dried over $MgSO_4$, and filtered. The solvent was evaporated and chromatography of the resulting solid on silica gel (95/5: hexane/EtOAc) gave the desired product (16.71 g, 54.4%). $MS(ES^-)$ m/e 257 $[M-H]^-$.

c) Methyl-2-benzyloxy-6-cyanobenzoate.

A solution of methyl-2-benzyloxy-6-hydroxybenzoate (2.730 g, 10.6 mmol) in methylene chloride (28.5 mL) at 0° C. under Ar was treated with N-phenyltrifluoromethanesulfonimide (4.5424 g, 12.7 mmol) and triethylamine (1.62 mL, 11.6 mmol). The reaction mixture was warmed up to rt, and stirred for 14 h. The solution was diluted with diethyl ether, and washed with water, 5% sodium hydroxide, and brine. The organic layer was dried over $MgSO_4$, filtered, and evaporated to give the crude triflate (4.476 g, 108%). $^1H$ NMR(250 MHz, CDCl$_3$) δ 7.35 (m, 6H), 6.95 (m, 2H), 5.16 (s, 2H), 3.94 (s, 3H). The crude triflate was dissolved in DMF (23 mL) and treated with palladium[0] tetrakistriphenylphosphine (0.3036 g, 0.260 mmol) and $Zn(CN)_2$ (1.1027 g, 9.39 mmol). The mixture was heated to 80° C. for 10 h. The reaction mixture was cooled to rt and poured into a solution of saturated sodium bicarbonate. The mixture was extracted with EtOAc, dried over $MgSO_4$, and filtered. The solvent was evaporated and chromatography of the resulting solid on silica gel (80/20: hexane/EtOAc) gave the desired product (2.20 g, 78% for two steps). $^1H$ NMR(250 MHz, CDCl$_3$) δ 7.5–7.2 (m, 8H), 5.19 (s, 2H), 4.00 (s, 3H)

d) Preparation of methyl-6-cyano-2-hydroxybenzoate.

To a solution of methyl-2-benzyloxy-6-cyanobenzoate (10.0 g, 37.4 mmol) in EtOAc (330 mL) under Ar, 10% Pd on carbon (4.72 g) was added. The reaction vessel was flushed with hydrogen, and the reaction mixture was allowed to stir at rt under hydrogen atmosphere at balloon pressure. After 3 h the reaction was flushed with Ar, and the solution was filtered through celite. The solvent was evaporated resulting in the desired product (6.12 g, 92.2%). Anal. Calcd. For $C_9H_7NO_3$: C, 61.02; H, 3.98; N, 7.91. Found C, 60.74; H, 3.99: N, 7.65.

e) Preparation of methyl-6-cyano-2-hydroxy-3-nitrobenzoate.

A suspension of methyl-6-cyano-2-hydroxybenzoate (1.1428 g, 6.45 mmol) in acetic anhydride (21 mL) at 0° C. was treated dropwise with concentrated nitric acid (0.41 mL, 6.44 mmol). The mixture was allowed to warm up to rt during which time all of the starting material dissolved. The solution was stirred for 36 h, then poured into water and extracted with EtOAc. The combined organic layers were dried over $MgSO_4$ and filtered. The solvent was evaporated and chromatography of the resulting solid on silica gel (70/30/1: hexane/EtOAc/HOAc) gave the desired product (0.50 g, 35.7%). $MS(ES^-)$ m/e 221 $[M-H]^-$.

f) Methyl-3-amino-6-cyano-2-hydroxybenzoate.

To a solution of methyl-6-cyano-2-hydroxy-3-nitrobenzoate (402 mg, 1.8 1 mmol) in EtOAc (40 mL) under Ar, 10% Pd on carbon (0.23 g) was added. The reaction vessel was flushed with hydrogen, and the reaction mixture was allowed to stir at rt under a hydrogen atmosphere at balloon pressure. After 2 h the reaction was flushed with Ar, and then the solution was filtered through celite. The solvent was evaporated resulting in the desired product (334 mg, 96.0%). $MS(ES^-)$ m/e 192 $[M-H]^-$.

g) N-(2-bromophenyl)-N'-(4-cyano-2-hydroxy-3-methoxycarbonylphenyl)-N"-cyanoguanidine Following the procedure of Example2(a)–1(e), except substituting Methyl-3-amino-6-cyano-2-hydroxybenzoate for 5-cyano-2-nitro-phenol, the title compound was prepared (19% overall,). $^1H$ NMR(400 MHz, DMSO $d_6$) δ 11.08 (s, 1H), 9.69 (s, 1H), 8.89 (s, 1H), 7.99 (d, J=8.40 Hz, 1H), 7.73 (d, J=7.9 Hz, 1H), 7.50–7.42 (m, 3H), 7.28 (t, 1H); IR(KBr)

2228, 2186cm$^{-1}$IR(KBr) 2225,2177 cm$^{-1}$; MS(ES$^-$) m/e 412, 414 [M–H]$^-$; mp 210–211° C.

METHOD OF TREATMENT

The compounds of Formula (I), or a pharmaceutically acceptable salt thereof can be used in the manufacture of a medicament for the prophylactic or therapeutic treatment of any disease state in a human, or other mammal, which is exacerbated or caused by excessive or unregulated IL-8 cytokine production by such mammal's cell, such as but not limited to monocytes and/or macrophages, or other chemokines which bind to the IL-8 α or β receptor, also referred to as the type I or type II receptor.

Accordingly, the present invention provides a method of treating a chemokine mediated disease, wherein the chemokine is one which binds to an IL-8 α or β receptor and which method comprises administering an effective amount of a compound of Formula (I) or a pharmaceutically acceptable salt thereof. In particular, the chemokines are IL-8, GROα, GROβ, GROγ, ENA-78 or NAP-2.

The compounds of Formula (I) are administered in an amount sufficient to inhibit cytokine function, in particular IL-8, GROα, GROβ, GROγ, ENA-78 or NAP-2, such that they are biologically regulated down to normal levels of physiological function, or in some case to subnormal levels, so as to ameliorate the disease state. Abnormal levels of IL-8, GROα, GROβ, GROγ, ENA-78 or NAP-2 for instance in the context of the present invention, constitute: (i) levels of free IL-8 greater than or equal to 1 picogram per mL; (ii) any cell IL-8, GROα, GROβ, GROγ, ENA-78 or NAP-2 above normal physiological levels; or (iii) the presence of IL-8, GROα, GROβ, GROγ, ENA-78 or NAP-2 above basal levels in cells or tissues in which IL-8, GROα, GROβ, GROγ, ENA-78 or NAP-2 respectively, is produced.

There are many disease states in which excessive or unregulated IL-8 production is implicated in exacerbating and/or causing the disease. Chemokine mediated diseases include psoriasis, atopic dermatitis, arthritis, asthma, chronic obstructive pulmonary disease, adult respiratory distress syndrome, inflammatory bowel disease, Crohn's disease, ulcerative colitis, stroke, septic shock, endotoxic shock, gram negative sepsis, toxic shock syndrome, cardiac and renal reperfusion injury, glomerulonephritis, thrombosis, graft vs. host reaction, alzheimers disease, allograft rejections, malaria, restinosis, angiogenesis or undesired hematopoietic stem cells release.

These diseases are primarily characterized by massive neutrophil infiltration, T-cell infiltration, or neovascular growth, and are associated with increased IL-8, GROα, GROβ, GROγ or NAP-2 production which is responsible for the chemotaxis of neutrophils into the inflammatory site or the directional growth of endothelial cells. In contrast to other inflammatory cytokines (IL-1, TNF, and IL-6), IL-8, GROα, GROβ, GROγ or NAP-2 has the unique property of promoting neutrophil chemotaxis, enzyme release including but not limited to elastase release as well as superoxide production and activation. The α-chemokines but particularly, GROα, GROβ, GROγ or NAP-2, working through the IL-8 type I or II receptor can promote the neovascularization of tumors by promoting the directional growth of endothelial cells. Therefore, the inhibition of IL-8 induced chemotaxis or activation would lead to a direct reduction in the neutrophil infiltration.

Recent evidence also implicates the role of chemokines in the treatment of HIV infections, Littleman et al., Nature 381, pp 661 (1996) and Koup et al., Nature 381, pp 667 (1996).

The present invention also provides for a means of treating, in an acute setting, as well as preventing, in those individuals deemed susceptible to, CNS injuries by the chemokine receptor antagonist compounds of Formula (I).

CNS injuries as defined herein include both open or penetrating head trauma, such as by surgery, or a closed head trauma injury, such as by an injury to the head region. Also included within this definition is ischemic stroke, particularly to the brain area.

Ischemic stroke may be defined as a focal neurologic disorder that results from insufficient blood supply to a particular brain area, usually as a consequence of an embolus, thrombi, or local atheromatous closure of the blood vessel. The role of inflammatory cytokines in this are has been emerging and the present invention provides a mean for the potential treatment of these injuries. Relatively little treatment, for an acute injury such as these has been available.

TNF-α is a cytokine with proinflammatory actions, including endothelial leukocyte adhesion molecule expression. Leukocytes infiltrate into ischemic brain lesions and hence compounds which inhibit or decrease levels of TNF would be useful for treatment of ischemic brain injury. See Liu et al., Stoke, Vol. 25. , No. 7, pp 1481–88 (1994) whose disclosure is incorporated herein by reference.

Models of closed head injuries and treatment with mixed 5-LO/CO agents is discussed in Shohami et al., J. of Vaisc & Clinical Physiology and Pharmacology, Vol. 3, No. 2, pp. 99–107 (1992) whose disclosure is incorporated herein by reference. Treatment which reduced edema formation was found to improve functional outcome in those animals treated.

The compounds of Formula (I) are administered in an amount sufficient to inhibit IL-8, binding to the IL-8 alpha or beta receptors, from binding to these receptors, such as evidenced by a reduction in neutrophil chemotaxis and activation. The discovery that the compounds of Formula (I) are inhibitors of IL-8 binding is based upon the effects of the compounds of Formulas (I) in the in vitro receptor binding assays which are described herein. The compounds of Formula (I) have been shown, in some instances, to be dual inhibitors of both recombinant type I and type II IL-8 receptors. Preferably the compounds are inhibitors of only one receptor, more preferably Type II.

As used herein, the term "IL-8 mediated disease or disease state" refers to any and all disease states in which IL-8, GROα, GROβ, GROγ, ENA-78 or NAP-2 plays a role, either by production of IL-8, GROα, GROβ, GROγ, ENA-78 or NAP-2 themselves, or by IL-8, GROα, GROβ, GROγ, ENA-78 or NAP-2 causing another monokine to be released, such as but not limited to IL-1, IL-6 or TNF. A disease state in which, for instance, IL-1 is a major component, and whose production or action, is exacerbated or secreted in response to IL-8, would therefore be considered a disease stated mediated by IL-8.

As used herein, the term "chemokine mediated disease or disease state" refers to any and all disease states in which a chemokine which binds to an IL-8α or β receptor plays a role, such as but not limited IL-8, GROα, GROβ, GROγ, ENA-78 or NAP-2. This would include a disease state in which, IL-8 plays a role, either by production of IL-8 itself, or by IL-8 causing another monokine to be released, such as but not limited to IL-1, IL-6 or TNF. A disease state in which, for instance, IL-1 is a major component, and whose production or action, is exacerbated or secreted in response to IL-8, would therefore be considered a disease stated mediated by IL-8.

As used herein, the term "cytokine" refers to any secreted polypeptide that affects the functions of cells and is a molecule which modulates interactions between cells in the immune, inflammatory or hematopoietic response. A cytokine includes, but is not limited to, monokines and lymphokines, regardless of which cells produce them. For instance, a monokine is generally referred to as being produced and secreted by a mononuclear cell, such as a macrophage and/or monocyte. Many other cells however also produce monokines, such as natural killer cells, fibroblasts, basophils, neutrophils, endothelial cells, brain astrocytes, bone marrow stromal cells, epideral keratinocytes and B-lymphocytes. Lymphokines are generally referred to as being produced by lymphocyte cells. Examples of cytokines include, but are not limited to, Interleukin-1 (IL-1), Interleukin-6 (IL-6), Interleukin-8 (IL-8), Tumor Necrosis Factor-alpha (TNF-α) and Tumor Necrosis Factor beta (TNF-β).

As used herein, the term "chemokine" refers to any secreted polypeptide that affects the functions of cells and is a molecule which modulates interactions between cells in the immune, inflammatory or hematopoietic response, similar to the term "cytokine" above. A chemokine is primarily secreted through cell transmembranes and causes chemotaxis and activation of specific white blood cells and leukocytes, neutrophils, monocytes, macrophages, T-cells, B-cells, endothelial cells and smooth muscle cells. Examples of chemokines include, but are not limited to, IL-8, GRO-α, GRO-β, GRO-γ, ENA-78, NAP-2, IP-10, MIP-1α, MIP-β, PF4, and MCP 1, 2, and 3.

In order to use a compound of Formula (I) or a pharmaceutically acceptable salt thereof in therapy, it will normally be formulated into a pharmaceutical composition in accordance with standard pharmaceutical practice. This invention, therefore, also relates to a pharmaceutical composition comprising an effective, non-toxic amount of a compound of Formula (I) and a pharmaceutically acceptable carrier or diluent.

Compounds of Formula (I), pharmaceutically acceptable salts thereof and pharmaceutical compositions incorporating such may conveniently be administered by any of the routes conventionally used for drug administration, for instance, orally, topically, parenterally or by inhalation. The compounds of Formula (I) may be administered in conventional dosage forms prepared by combining a compound of Formula (I) with standard pharmaceutical carriers according to conventional procedures. The compounds of Formula (I) may also be administered in conventional dosages in combination with a known, second therapeutically active compound. These procedures may involve mixing, granulating and compressing or dissolving the ingredients as appropriate to the desired preparation. It will be appreciated that the form and character of the pharmaceutically acceptable character or diluent is dictated by the amount of active ingredient with which it is to be combined, the route of administration and other well-known variables. The carrier(s) must be "acceptable" in the sense of being compatible with the other ingredients of the formulation and not deleterious to the recipient thereof.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time delay material well known to the art, such as glyceryl mono-stearate or glyceryl distearate alone or with a wax.

A wide variety of pharmaceutical forms can be employed. Thus, if a solid carrier is used, the preparation can be tableted, placed in a hard gelatin capsule in powder or pellet form or in the form of a troche or lozenge. The amount of solid carrier will vary widely but preferably will be from about 25 mg. to about 1 g. When a liquid carrier is used, the preparation will be in the form of a syrup, emulsion, soft gelatin capsule, sterile injectable liquid such as an ampule or nonaqueous liquid suspension.

Compounds of Formula (I) may be administered topically, that is by non-systemic administration. This includes the application of a compound of Formula (I) externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as liniments, lotions, creams, ointments or pastes, and drops suitable for administration to the eye, ear or nose. The active ingredient may comprise, for topical administration, from 0.001% to 10% w/w, for instance from 1% to 2% by weight of the formulation. It may however comprise as much as 10% w/w but preferably will comprise less than 5% w/w, more preferably from 0.1% to 1% w/w of the formulation.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy base. The base may comprise hydrocarbons such as hard, soft or liquid paraffin, glycerol, beeswax, a metallic soap; a mucilage; an oil of natural origin such as almond, corn, arachis, castor or olive oil; wool fat or its derivatives or a fatty acid such as steric or oleic acid together with an alcohol such as propylene glycol or a macrogel. The formulation may incorporate any suitable surface active agent such as an anionic, cationic or non-ionic surfactant such as a sorbitan ester or a polyoxyethylene derivative thereof. Suspending agents such as natural gums, cellulose derivatives or inorganic materials such as silicaceous silicas, and other ingredients such as lanolin, may also be included.

Drops according to the present invention may comprise sterile aqueous or oily solutions or suspensions and may be prepared by dissolving the active ingredient in a suitable aqueous solution of a bactericidal and/or fungicidal agent and/or any other suitable preservative, and preferably including a surface active agent. The resulting solution may then be clarified by filtration, transferred to a suitable container which is then sealed and sterilized by autoclaving or maintaining at 98–100° C. for half an hour. Alternatively, the solution may be sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Compounds of formula (I) may be administered parenterally, that is by intravenous, intramuscular, subcutaneous intranasal, intrarectal, intravaginal or intraperitoneal administration. The subcutaneous and intramuscular forms of parenteral administration are generally preferred. Appropriate dosage forms for such administration may be prepared by conventional techniques. Compounds of Formula (I) may also be administered by inhalation, that is by intranasal and oral inhalation administration. Appropriate dosage forms for such administration, such as an aerosol formulation or a metered dose inhaler, may be prepared by conventional techniques.

For all methods of use disclosed herein for the compounds of Formula (I), the daily oral dosage regimen will preferably be from about 0.01 to about 80 mg/kg of total body weight. The daily parenteral dosage regimen about 0.001 to about 80 mg/kg of total body weight. The daily topical dosage regimen will preferably be from 0.1 mg to 150 mg, administered one to four, preferably two or three times daily. The daily inhalation dosage regimen will preferably be from about 0.01 mg/kg to about 1 mg/kg per day. It will also be recognized by one of skill in the art that the optimal quantity and spacing of individual dosages of a compound of Formula (I) or a pharmaceutically acceptable salt thereof will be determined by the nature and extent of the condition being treated, the form, route and site of administration, and the particular patient being treated, and that such optimums can be determined by conventional techniques. It will also be appreciated by one of skill in the art that the optimal course of treatment, i.e., the number of doses of a compound of Formula (I) or a pharmaceutically acceptable salt thereof given per day for a defined number of days, can be ascertained by those skilled in the art using conventional course of treatment determination tests.

The invention will now be described by reference to the following biological examples which are merely illustrative and are not to be construed as a limitation of the scope of the present invention.

BIOLOGICAL EXAMPLES

The IL-8, and Gro-α chemokine inhibitiory effects of compounds of the present invention were determined by the following in vitro assay:

Receptor Binding Assays:

[$^{125}$I]IL-8 (human recombinant) was obtained from Amersham Corp., Arlington Heights, Ill., with specific activity 2000 Ci/mmol. Gro-α was obtained from NEN- New England Nuclear. All other chemicals were of analytical grade. High levels of recombinant human IL-8 type α and β receptors were individually expressed in Chinese hamster ovary cells as described previously (Holmes, et al., *Science*, 1991, 253, 1278). The Chinese hamster ovary membranes were homogenized according to a previously described protocol (Haour, et al., *J Biol Chem.*, 249 pp 2195–2205 (1974)). Except that the homogenization buffer was changed to 10mM Tris-HCL, 1mM MgS04, 0.5mM EDTA (ethylenediaminetetra-acetic acid), 1mMPMSF (α-toluenesulphonyl fluoride), 0.5 mg/L Leupeptin, pH 7.5. Membrane protein concentration was determined using Pierce Co. micro-assay kit using bovine serum albumin as a standard. All assays were performed in a 96-well micro plate format. Each reaction mixture contained $^{125}$I IL-8 (0.25 nM) or $^{125}$I Gro-α and 0.5 μg/mL of IL-8Rα or 1.0 μg/mL of IL-8Rβ membranes in 20 mM Bis-Trispropane and 0.4 mM Tris HCl buffers, pH 8.0, containing 1.2 mM MgSO$_4$, 0.1 mM EDTA, 25 mM NaCl and 0.03% CHAPS. In addition, drug or compound of interest was added which had been predissolved in DMSO so as to reach a final concentration of between 0.01 nM and 100 uM. The assay was initiated by addition of $^{125}$I-IL-8. After 1 hour at room temperature the plate was harvested using a Tomtec 96-well harvester onto a glass fiber filtermat blocked with 1% polyethylenimine/0.5% BSA and washed 3 times with 25 mM NaCl, 10 mM TrisHCl, 1 mM MgSO$_4$, 0.5 mM EDTA, 0.03% CHAPS, pH 7.4. The filter was then dried and counted on the Betaplate liquid scintillation counter. The recombinant IL-8 Rα, or Type I, receptor is also referred to herein as the non-permissive receptor and the recombinant IL-8 Rβ, or Type II, receptor is referred to as the permissive receptor.

The exemplified compounds of Formulas (I), Examples 1 to 11, noted herein in the Synthetic Chemistry Section demonstrated an IC$_{50}$ from about 5 to about 100 nM in the permissive models (IL-8b) for IL-8 receptor inhibition. A compound without an ionizable proton in the 2-position, N-(2-Allyloxy-4-cyano-phenyl)-N'-(2-bromophenyl)-N"-cyanoguanidine was found to be inactive in this assay.

Chemotaxis Assay:

The in vitro inhibitory properties of these compounds are determined in the neutrophil chemotaxis assay as described in Current Protocols in Immunology, vol I, Suppl 1, Unit 6.12.3., whose disclosure is incorporated herein by reference in its entirety. Neutrophils where isolated from human blood as described in Current Protocols in Immunology Vol I, Suppl 1 Unit 7.23.1, whose disclosure is incorporated herein by reference in its entirety. The chemoattractants IL-8, GRO-α, GRO-β, GRO-γ and NAP-2 are placed in the bottom chamber of a 48 multiwell chamber (Neuro Probe, Cabin John, Md) at a concentration between 0.1 and 100 nM. The two chambers are separated by a 5um polycarbonate filter. When compounds of this invention are tested, they are mixed with the cells (0.001–1000 nM) just prior to the addition of the cells to the upper chamber. Incubation is allowed to proceed for between about 45 and 90 min at about 37° C. in a humidified incubator with 5% CO$_2$. At the end of the incubation period, the polycarbonate membrane is removed and the top side washed, the membrane then stained using the Diff Quick staining protocol (Baxter Products, McGaw Park, Ill, USA). Cells which have chemotaxed to the chemokine are visually counted using a microscope. Generally, four fields are counted for each sample, these numbers are averaged to give the average number of cells which had migrated. Each sample is tested in triplicate and each compound repeated at least four times. To certain cells (positive control cells) no compound is added, these cells represent the maximum chemotactic response of the cells. In the case where a negative control (unstimulated) is desired, no chemokine is added to the bottom chamber. The difference between the positive control and the negative control represents the chemotactic activity of the cells.

Elastase Release Assay:

The compounds of this invention are tested for their ability to prevent Elastase release from human neutrophils. Neutrophils are isolated from human blood as described in Current Protocols in Immunology Vol I, Suppl 1 Unit 7.23.1. PMNs 0.88×10$^6$ cells suspended in Ringer's Solution (NaCl 118, KCl 4.56, NaHCO3 25, KH2PO4 1.03, Glucose 11.1, HEPES 5 mM, pH 7.4) are placed in each well of a 96 well plate in a volume of 50 μl. To this plate is added the test compound (0.001–1000 nM) in a volume of 50 μl, Cytochalasin B in a volume of 50 μl (20 μg/ml) and Ringers buffer in a volume of 50 μl. These cells are allowed to warm (37° C., 5% CO2, 95% RH) for 5 min before IL-8, GROα, GROβ, GROγ or NAP-2 at a final concentration of 0.01–1000 nM was added. The reaction is allowed to proceed for 45 min before the 96 well plate is centrifuged (800×g 5 min) and 100 μl of the supernatant removed. This suppernatant is added to a second 96 well plate followed by an artificial elastase substrate (MeOSuc-Ala-Ala-Pro-Val-AMC, Nova Biochem, La Jolla, Calif.) to a final concentration of 6 μg/ml dissolved in phosphate buffered saline. Immediately, the plate is placed in a fluorescent 96 well plate reader (Cytofluor 2350, Millipore, Bedford, Mass.) and data collected at 3 min intervals according to the method of Nakajima et al J. Biol Chem 254 4027 (1979). The amount of Elastase released from the PMNs is calculated by measuring the rate of MeOSuc-Ala-Ala-Pro-Val-AMC degradation.

TNF-α in Traumatic Brain Injury Assay

The present assay provides for examination of the expression of tumor necrosis factor mRNA in specific brain regions which follow experimentally induced lateral fluid-percussion traumatic brain injury (TBI) in rats. Adult Sprague-Dawley rats (n=42) were anesthetized with sodium pentobarbital (60 mg/kg, i.p.) and subjected to lateral fluid-percussion brain injury of moderate severity (2.4 atm.) centered over the left temporaparietal cortex (n=18), or "sham" treatment (anesthesia and surgery without injury, n=18). Animals are sacrificed by decapitation at 1, 6 and 24 hr. post injury, brains removed, and tissue samples of left (injured) parietal cortex (LC), corresponding area in the contralateral right cortex (RC), cortex adjacent to injured parietal cortex (LA), corresponding adjacent area in the right cortex (RA), left hippocampus (LH) and right hippocampus (RH) are prepared. Total RNA was isolated and Northern blot hybridization is performed and quantitated relative to an TNF-α positive control RNA (macrophage=100%). A marked increase of TNF-α mRNA expression is observed in LH (104±17% of positive control, p<0.05 compared with sham), LC (105±21%, p<0.05) and LA (69±8%, p<0.01) in the traumatized hemisphere 1 hr. following injury. An increased TNF-α mRNA expression is also observed in LH (46±8%, p <0.05), LC (30±3%, p <0.01) and LA (32±3%, p<0.01) at 6 hr. which resolves by 24 hr. following injury. In the contralateral hemisphere, expression of TNF-α mRNA is increased in RH (46±2%, p<0.01), RC (4±3%) and RA (22±8%) at 1 hr. and in RH (28±11%), RC (7±5%) and RA (26±6%, p<0.05) at 6 hr. but not at 24 hr. following injury. In sham (surgery without injury) or naive animals, no consistent changes in expression of TNF-α mRNA are observed in any of the 6 brain areas in either hemisphere at any times. These results indicate that following parasagittal fluid-percussion brain injury, the temporal expression of TNF-α mRNA is altered in specific brain regions, including those of the non-traumatized hemisphere. Since TNF-α is able to induce nerve growth factor (NGF) and stimulate the release of other cytokines from activated astrocytes, this post-traumatic alteration in gene expression of TNF-α plays an important role in both the acute and regenerative response to CNS trauma.

CNS Injury model for IL-β mRNA

This assay characterizes the regional expression of interleukin-1β (IL-1β) mRNA in specific brain regions following experimental lateral fluid-percussion traumatic brain injury (TBI) in rats. Adult Sprague-Dawley rats (n=42) are anesthetized with sodium pentobarbital (60 mg/kg, i.p.) and subjected to lateral fluid-percussion brain injury of moderate severity (2.4 atm.) centered over the left temporaparietal cortex (n=18), or "sham" treatment (anesthesia and surgery without injury). Animals are sacrificed at 1, 6 and 24 hr. post injury, brains removed, and tissue samples of left (injured) parietal cortex (LC), corresponding area in the contralateral right cortex (RC), cortex adjacent to injured parietal cortex (LA), corresponding adjacent area in the right cortex (RA), left hippocampus (LH) and right hippocampus (RH) are prepared. Total RNA is isolated and Northern blot hybridization was performed and the quantity of brain tissue IL-1β mRNA is presented as percent relative radioactivity of IL-1β positive macrophage RNA which was loaded on same gel. At 1 hr. following brain injury, a marked and significant increase in expression of IL-1β mRNA is observed in LC (20.0±0.7% of positive control, n=6, p<0.05 compared with sham animal), LH (24.5±0.9%, p<0.05) and LA (21.5±3.1%, p<0.05) in the injured hemisphere, which remained elevated up to 6 hr. post injury in the LC (4.0±0.4%, n=6, p <0.05) and LH (5.0±1.3%, p<0.05). In sham or naive animals, no expression of IL-1β mRNA is observed in any of the respective brain areas. These results indicate that following TBI, the temporal expression of IL-1β mRNA is regionally stimulated in specific brain regions. These regional changes in cytokines, such as IL-1β play a role in the post-traumatic.

The above description fully discloses the invention including preferred embodiments thereof. Modifications and improvements of the embodiments specifically disclosed herein are within the scope of the following claims. Without further elaboration, it is believed that one skilled in the are can, using the preceding description, utilize the present invention to its fullest extent. Therefore the Examples herein are to be construed as merely illustrative and not a limitation of the scope of the present invention in any way. The embodiments of the invention in which an exclusive property or privilege is claimed are defined as follows.

What is claimed is:

1. A method of treating a chemokine mediated disease state, wherein the chemokine binds to an IL-8 α or β receptor in a mammal, which comprises administering to said mammal an effective amount of a compound of the formula:

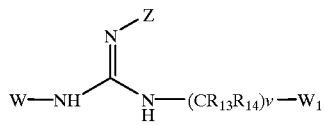

wherein

Z is cyano, $OR_{11}$, $C(O)NR_{15}R_{16}$, $R_{18}$, $C(O)R_{11}$, $C(O)OR_{11}$, or $S(O)_2R_{17}$;

R is any functional moiety having an ionizable hydrogen and a pKa of 10 or less;

$R_1$ is independently selected from hydrogen; halogen; nitro; cyano; halosubstituted $C_{1-10}$ alkyl; $C_{1-10}$ alkyl; $C_{2-10}$ alkenyl; $C_{1-10}$ alkoxy; halosubstituted$C_{1-10}$ alkoxy; azide; $(CR_8R_8)q$ $S(O)_tR_4$; hydroxy; hydroxy$C_{1-4}$alkyl; aryl; aryl$C_{1-4}$alkyl; aryloxy; aryl $C_{1-4}$ alkyloxy; heteroaryl; heteroarylalkyl; heterocyclic, heterocyclic $C_{1-4}$alkyl; heteroaryl $C_{1-4}$ alkyloxy; aryl $C_{2-10}$ alkenyl; heteroaryl $C_{2-10}$ alkenyl; heterocyclic $C_{2-10}$ alkenyl; $(CR_8R_8)qNR_4R_5$; $C_{2-10}$alkenylC(O)$NR_4R_5$; $(CR_8R_8)q$ $C(O)NR_4R_5$; $(CR_8R_8)qC(O)NR_4R_{10}$; $S(O)_3R_8$; $(CR_8R_8)q$ $C(O)R_{11}$;

C$_{2-10}$alkenyl C(O)R$_{11}$; C$_{2-10}$alkenylC(O)OR$_{11}$; (CR$_8$R$_8$)q C(O)OR$_{12}$; (CR$_8$R$_8$)q OC(O) R$_{11}$; (CR$_8$R$_8$) qNR$_4$C(O)R$_{11}$; (CR$_8$R$_8$)qNHS(O)$_2$R$_{19}$; (CR$_8$R$_8$)q S(O)$_2$ NR$_4$R$_5$; or two R$_1$ moieties together may form O—(CH$_2$)$_s$O— or a 5 to 6 membered saturated or unsaturated ring, and wherein the aryl, heteroaryl and heterocyclic moieties may be optionally substituted;

q is 0, or an integer having a value of 1 to 10;

t is 0, or an integer having a value of 1 or 2;

s is an integer having a value of 1 to 3;

v is 0, or an integer having a value of 1 to 4;

R$_4$ and R$_5$ are independently hydrogen, optionally substituted C$_{1-4}$ alkyl, optionally substituted aryl, optionally substituted aryl C$_{1-4}$alkyl, optionally substituted heteroaryl, optionally substituted heteroaryl C$_{1-4}$alkyl, heterocyclic, heterocyclic C$_{1-4}$ alkyl, or R$_4$ and R$_5$ together with the nitrogen to which they are attached form a 5 to 7 member ring which may optionally comprise an additional heteroatom selected from oxygen, nitrogen or sulfur;

Y is independently selected from hydrogen; halogen; nitro; cyano; halosubstituted C$_{1-10}$ alkyl; C$_{1-10}$ alkyl; C$_{2-10}$ alkenyl; C$_{1-10}$ alkoxy; halosubstitutedC$_{1-10}$alkoxy; azide; (CR$_8$R$_8$)q S(O)$_t$R$_4$; hydroxy; hydroxyC$_{1-4}$alkyl; aryl; arylC$_{1-4}$alkyl; aryloxy; arylC$_{1-4}$ alkyloxy; heteroaryl; heteroarylalkyl; heteroarylC$_{1-4}$alkyloxy; heterocyclic, heterocyclic C$_{1-4}$alkyl; arylC$_{2-10}$ alkenyl; heteroarylC$_{2-10}$ alkenyl; heterocyclic C$_{2-10}$ alkenyl; (CR$_8$R$_8$)qNR$_4$R$_5$; C$_{2-10}$ alkenyl C(O)NR$_4$R$_5$; (CR$_8$R$_8$)q C(O)NR$_4$R$_5$; (CR$_8$R$_8$)qC (O)NR$_4$R$_{10}$; S(O)$_3$R$_8$; (CR$_8$R$_8$)q C(O)R$_{11}$; C$_{2-10}$alkenylC(O)R$_{11}$; C$_{2-10}$ alkenyl C(O)OR$_{11}$; C(O) R$_{11}$; (CR$_8$R$_8$)qC(O)OR$_{12}$; (CR$_8$R$_8$)qOC(O) R$_{11}$; (CR$_8$R$_8$)q NR$_4$C(O)R$_{11}$; (CR$_8$R$_8$)qNHS(O)$_2$R$_d$; (CR$_8$R$_8$)q S(O)$_2$NR$_4$R$_5$; or two Y moieties together may form O—(CH$_2$)$_s$O— or a 5 to 6 membered saturated or unsaturated ring, and wherein the aryl, heteroaryl and heterocyclic moieties may be optionally substituted;

n is an integer having a value of 1 to 3;

m is an integer having a value of 1 to 3;

R$_6$ and R$_7$ are independently hydrogen or a C$_{1-4}$ alkyl group; or R$_6$ and R$_7$ together with the nitrogen to which they are attached form a 5 to 7 member ring which ring may optionally contain an additional heteroatom selected from oxygen, nitrogen or sulfur;

R$_8$ is independently selected from hydrogen or C$_{1-4}$ alkyl;

R$_{10}$ is C$_{1-10}$ alkyl C(O)$_2$R$_8$;

R$_{11}$ is hydrogen, C$_{1-4}$ alkyl, optionally substituted aryl, optionally substituted aryl C$_{1-4}$alkyl, optionally substituted heteroaryl, optionally substituted heteroarylC$_{1-4}$ alkyl, optionally substituted heterocyclic, or optionally substituted heterocyclicC$_{1-4}$alkyl;

R$_{12}$ is hydrogen, C$_{1-10}$ alkyl, optionally substituted aryl or optionally substituted arylalkyl;

R$_{13}$ and R$_{14}$ are independently hydrogen, optionally substituted C$_{1-4}$ alkyl or one of R$_{13}$ and R$_{14}$ may be optionally substituted aryl;

R$_{15}$ and R$_{16}$ are independently hydrogen, optionally substituted C$_{1-4}$ alkyl, optionally substituted aryl, optionally substituted aryl C$_{1-4}$alkyl, optionally substituted heteroaryl, optionally substituted heteroarylC$_{1-4}$alkyl, optionally substituted heterocyclic, optionally substituted heterocyclicC$_{1-4}$alkyl, or R$_{15}$ and R$_{16}$ may together with the nitrogen to which they are attached form a 5 to 7 member ring optionally containing an additional heteroatom selected from oxygen, nitrogen, or sulfur;

R$_{17}$ is C$_{1-4}$ alkyl, NR$_{15}$R$_{16}$, OR$_{11}$, optionally substituted aryl, optionally substituted aryl C$_{1-4}$alkyl, optionally substituted heteroaryl, optionally substituted heteroarylC$_{1-4}$alkyl, optionally substituted heterocyclic, or optionally substituted heterocyclicC$_{1-4}$alkyl;

R$_{18}$ is optionally substituted C$_{1-4}$ alkyl, optionally substituted aryl, optionally substituted aryl C$_{1-4}$alkyl, optionally substituted heteroaryl, optionally substituted heteroarylC$_{1-4}$alkyl, optionally substituted heterocyclic, or optionally substituted heterocyclicC$_{1-4}$ alkyl;

R$_{19}$ is C$_{1-4}$alkyl, aryl, arylalkyl, heteroaryl, heteroarylC$_{1-4}$alkyl, heterocyclic, or heterocyclicC$_{1-4}$alkyl, wherein the all of these moieties may be optionally substituted;

R$_d$ is NR$_6$R$_7$, alkyl, arylC$_{1-4}$ alkyl, arylC$_{2-4}$ alkenyl, heteroaryl, hetroaryl—C$_{1-4}$alkyl, heteroarylC$_{2-4}$ alkenyl, heterocyclic, heterocyclicC$_{1-4}$ alkyl, wherein the alkyl, aryl, arylalkyl, heteroaryl, heteroaryl alkyl, heterocyclic, and heterocyclic alkyl rings may be optionally substituted;

W is 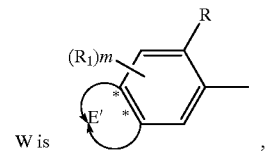, 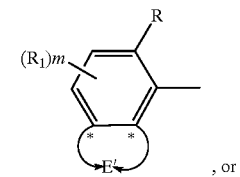, or 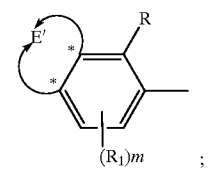;

the E' containing ring may be absent or present, and when present, is selected from

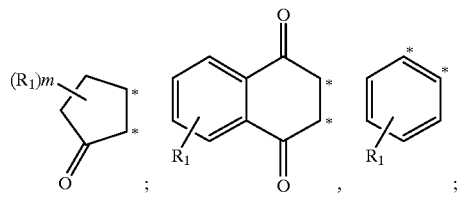

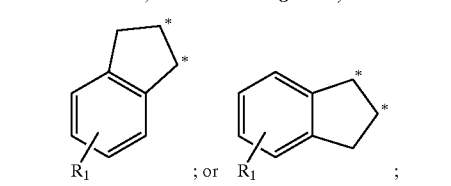

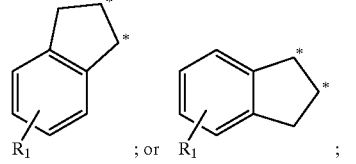

-continued
the asterix * denoting point of attachment of the ring;

$W_1$ is 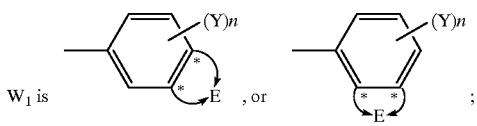

the E containing ring may be absent or present, and when present, is selected from

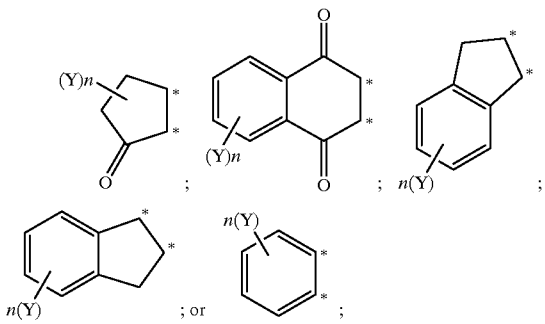

the asterix * denoting point of attchment of the ring;

or a pharmaceutically acceptable salt thereof.

2. The method according to claim 1 wherein the ionizable hydrogen has a pKa of 3 to 10.

3. The method according to claim 2 wherein R is hydroxy, carboxylic acid, thiol, $SR_2$, $OR_2$, NH—$C(O)R_a$, $C(O)NR_6R_7$, $NHS(O)_2R_b$, $S(O)_2NHR_c$, $NHC(X_2)NHR_b$, or tetrazolyl;

wherein $R_2$ is a substituted aryl, heteroaryl, or heterocyclic moiety which ring has the functional moiety providing the ionizable hydrogen having a pKa of 10 or less;

$R_{6'}$ and $R_{7'}$ are hydrogen, $C_{1-4}$ alkyl, aryl, aryl$C_{1-4}$alkyl, aryl$C_{2-4}$alkenyl, heteroaryl, heteroaryl$C_{1-4}$alkyl, heteroaryl$C_{2-4}$ alkenyl, heterocyclic, heterocyclic $C_{1-4}$alkyl, heterocyclic $C_{2-4}$alkenyl moiety, all of which may be optionally substituted one to three times independently by halogen; nitro; halosubstituted $C_{1-4}$ alkyl, such as $CF_3$; $C_{1-4}$ alkyl, such as methyl; $C_{1-4}$ alkoxy, such as methoxy; $NR_9C(O)R_a$; $C(O)NR_6R_7$, $S(O)_3H$, or $C(O)OC_{1-4}$ alkyl, provided that one of $R_{6'}$ and $R_{7'}$ are hydrogen, but not both;

$R_a$ is an aryl, aryl $C_{1-4}$alkyl, heteroaryl, heteroaryl $C_{1-4}$alkyl, heterocyclic, or a heterocyclic $C_{1-4}$alkyl moiety, all of which may be optionally substituted;

$R_b$ is a $NR_6R_7$, alkyl, aryl, aryl$C_{1-4}$alkyl, aryl$C_{2-4}$alkenyl, heteroaryl, heteroaryl$C_{1-4}$alkyl, heteroaryl$C_{2-4}$ alkenyl, heterocyclic, heterocyclic $C_{1-4}$alkyl, heterocyclic $C_{2-4}$alkenyl moiety, camphor, all of which may be optionally substituted one to three times independently by halogen; nitro; halosubstituted $C_{1-4}$ alkyl; $C_{1-4}$ alkyl; $C_{1-4}$ alkoxy; $NR_9C(O)R_a$; $C(O)NR_6R_7$, $S(O)_3H$, or $C(O)OC_{1-4}$ alkyl;

$R_9$ is hydrogen or a $C_{1-4}$ alkyl;

$R_c$ is alkyl, aryl, aryl$C_{1-4}$alkyl, aryl$C_{2-4}$alkenyl, heteroaryl, heteroaryl$C_{1-4}$alkyl, heteroaryl$C_{2-4}$alkenyl, heterocyclic, heterocyclic $C_{1-4}$alkyl, or a heterocyclic $C_{2-4}$alkenyl moiety, all of which may be optionally substituted one to three times independently by halogen, nitro, halosubstituted $C_{1-4}$ alkyl, $C_{1-4}$ alkyl, $C_{1-4}$ alkoxy, $NR_9C(O)R_a$, $C(O)NR_6R_7$, $S(O)_3H$, or $C(O)OC_{1-4}$ alkyl; and $X_2$ is oxygen or sulfur.

4. The method according to claim 3 wherein the $R_2$ is optionally substituted one to three times by halogen, nitro, halosubstituted $C_{1-10}$ alkyl, $C_{1-10}$ alkyl, $C_{1-10}$ alkoxy, hydroxy, SH, $C(O)NR_6R_7$, NH—$C(O)R_a$, $NHS(O)_2R_b$, $S(O)NR_6R_7$, $C(O)OR_8$, or a tetrazolyl ring.

5. The method according to claim 3 wherein R is OH, —$NHS(O)_2R_b$ or $C(O)OH$.

6. The method according to claim 1 wherein $R_1$ is halogen, cyano, nitro, $CF_3$, $C(O)NR_4R_5$, alkenyl $C(O)NR_4R_5$, $C(O)$ $R_4R_{10}$, alkenyl $C(O)OR_{12}$, heteroaryl, heteroarylalkyl, heteroaryl alkenyl, or $S(O)NR_4R_5$.

7. The method according to claim 1 wherein Y is halogen, $C_{1-4}$ alkoxy, optionally substituted aryl, optionally substituted arylalkoxy, methylene dioxy, $NR_4R_5$, thio$C_{1-4}$alkyl, thioaryl, halosubstituted alkoxy, optionally substituted $C_{1-4}$alkyl, or hydroxy alkyl.

8. The method according to claim 1 wherein R is OH, SH, or $NHS(O)_2R_b$, and $R_1$ is substituted in the 3-position, the 4-position or di substituted in the 3,4-position by an electron withdrawing moiety.

9. The method according to claim 1 wherein the mammal is afflicted with a chemokine mediated disease selected from psoriasis, atopic dermatitis, asthma, chronic obstructive pulmonary disease, adult respiratory distress syndrome, arthritis, inflammatory bowel disease, Crohn's disease, ulcerative colitis, septic shock, endotoxic shock, gram negative sepsis, toxic shock syndrome, stroke, cardiac and renal reperfusion injury, glomerulo-nephritis, thrombosis, Alzheimer's disease, graft vs. host reaction, or allograft rejections.

10. The method according to claim 1 wherein the compound is:

N-(2-Hydroxy-4-nitrophenyl)-N'-(2-chlorophenyl)-N"-cyanoguanidine

N-(2-Hydroxy 4-nitro phenyl) N'-(2-chloro phenyl)-N"-cyano guanidine

N-(4-Cyano-2-hydroxyphenyl)-N'-(phenyl (cyanoguanidine

N-(2-Bromophenyl) N'-(4-cyano-2-hydroxyphenyl) N"-cyanoguanidine

N-(4-Cyano-2-hydroxyphenyl)-N'-(2,3-dichlorophenyl)-N"-cyanoguanidine

N-(2-Bromophenyl)-N'-(4-cyano-2-hydroxy-3-propylphenyl)-N"-cyanoguanidine

N-(2-Bromophenyl)-N'-(4-cyano-2-hydroxy-3-isobutylphenyl)-N"-cyanoguanidine

N-(2-Bromophenyl)-N'-(3-bromo-4-cyano-2-hydroxyphenyl)-N"-cyanoguanidine

N-(4-Cyano-2-hydroxy-3-propylphenyl)-N'-(2,3-dichlorophenyl)-N"-cyanoguanidine

N-(3-Bromo-4-cyano-2-hydroxyphenyl)-N'-(2,3-methylenedioxyphenyl)-N"-cyanoguanidine N-(2-Chlorophenyl)-N'-(4-cyano-2-hydroxy-3-propylphenyl)-N"-cyanoguanidine N-(2-Bromophenyl)-N'-(4-cyano-2-hydroxy-3-methoxycarbonylphenyl)-N"-cyanoguanidine;

or a pharmaceutically acceptable salt thereof.

* * * * *